US008657762B2

(12) United States Patent
Takashima et al.

(10) Patent No.: US 8,657,762 B2
(45) Date of Patent: Feb. 25, 2014

(54) BLOOD TEST DEVICE

(75) Inventors: Tetsuya Takashima, Ehime (JP); Masaki Fujiwara, Ehime (JP); Takeshi Nishida, Fukuoka (JP); Yoshinori Amano, Ehime (JP); Toshiki Matsumoto, Ehime (JP); Kenichi Hamanaka, Ehime (JP); Keisuke Matsumura, Ehime (JP); Yohei Hashimoto, Ehime (JP)

(73) Assignee: Panasonic Corporation, Osaka (JP)

( * ) Notice: Subject to any disclaimer, the term of this patent is extended or adjusted under 35 U.S.C. 154(b) by 889 days.

(21) Appl. No.: 12/669,254

(22) PCT Filed: Jul. 18, 2008

(86) PCT No.: PCT/JP2008/001939
§ 371 (c)(1),
(2), (4) Date: Jan. 15, 2010

(87) PCT Pub. No.: WO2009/011137
PCT Pub. Date: Jan. 22, 2009

(65) Prior Publication Data
US 2010/0222703 A1    Sep. 2, 2010

(30) Foreign Application Priority Data

| Jul. 18, 2007 | (JP) | 2007-186636 |
| Jul. 18, 2007 | (JP) | 2007-186637 |
| Jul. 18, 2007 | (JP) | 2007-186638 |
| Jul. 18, 2007 | (JP) | 2007-186639 |
| Jul. 18, 2007 | (JP) | 2007-186642 |
| Jan. 16, 2008 | (JP) | 2008-006588 |

(51) Int. Cl.
*A61B 5/00*    (2006.01)

(52) U.S. Cl.
USPC .......................................... 600/583; 600/584

(58) Field of Classification Search
USPC ................... 600/583, 584, 573; 606/181–183
See application file for complete search history.

(56) References Cited

U.S. PATENT DOCUMENTS

| 5,971,941 | A  | * | 10/1999 | Simons et al. | 600/573 |
| 6,183,489 | B1 | * | 2/2001  | Douglas et al. | 606/181 |
| 2004/0215224 | A1 | * | 10/2004 | Sakata et al. | 606/181 |
| 2005/0015020 | A1 | * | 1/2005  | LeVaughn et al. | 600/583 |

(Continued)

FOREIGN PATENT DOCUMENTS

| CA | 2448584 | 10/2003 |
| CA | 2480747 | 10/2003 |

(Continued)

*Primary Examiner* — Brian Szmal
*Assistant Examiner* — H. Q. Nguyen
(74) *Attorney, Agent, or Firm* — Greenblum & Bernstein P.L.C.

(57) ABSTRACT

A blood test device (21) ensuring successful measurement wherein fingers scarcely slip out from the blood test device and blood never sticks to other sites in the course from the puncture of the patient's skin to the completion of the blood test. This blood test device (21) comprises a cartridge (24) in which sensors (23) pooling blood oozing out from the punctured skin are stored in a layered state, a transport unit transporting a single sensor sheet (23) from the inside of the cartridge (24) to the outside, a holder (25) holding the transported sensor (23), a laser emitting unit (26) puncturing the skin in the state where the sensor (23) is held by the holder (25), and a pump (28) keeping the inside of the holder (25) and the inside of the cartridge (24) under negative pressure.

31 Claims, 40 Drawing Sheets

(56) References Cited

U.S. PATENT DOCUMENTS

| | | |
|---|---|---|
| 2007/0293790 A1 | 12/2007 | Bainczyk et al. |
| 2009/0177117 A1 | 7/2009 | Amano et al. |
| 2009/0281455 A1 | 11/2009 | Fujiwara et al. |
| 2009/0318834 A1 | 12/2009 | Fujiwara et al. |
| 2010/0068795 A1 | 3/2010 | Shinohara et al. |

FOREIGN PATENT DOCUMENTS

| | | |
|---|---|---|
| JP | 2003-524496 | 8/2003 |
| JP | 2004-519302 | 7/2004 |
| JP | 2005-522243 | 7/2005 |
| WO | 01/64105 | 9/2001 |
| WO | 02/078533 | 10/2002 |
| WO | 03/083469 | 10/2003 |
| WO | 2006/058653 | 6/2006 |

* cited by examiner

BLOOD TEST DEVICE

TECHNICAL FIELD

The present invention relates to a blood test apparatus for testing, for example, the property of blood.

BACKGROUND ART

Diabetes patients need to measure their blood sugar level on a regular basis and inject insulin based on the measured blood sugar level to maintain a normal blood sugar level. To maintain this normal blood sugar level, diabetes patients need to measure the blood sugar level on a regular basis. Therefore, patients puncture the skin of their fingers and so forth by using a blood test apparatus, sample a small amount of blood exuding from the skin and analyze the components, such as blood sugar level, based on the sampled blood.

Conventionally, the blood test apparatus disclosed in Patent Document 1 has been known. Now, the procedure of a blood test using the blood test apparatus disclosed in Patent Document 1 will be described.

First, the patient touches the blood test apparatus with a finger of one hand (e.g. the index finger of the left hand), pushing a puncturing button of the blood test apparatus by the other hand (e.g. the right hand) and ejecting a puncture needle from a lancet to puncture the skin, so that a droplet of blood is formed on the surface of the skin. Next, the patient brings one of blood sensors stacked and stored in a cartridge installed in the blood test apparatus close to the puncturing position to make the sensor touch the blood. By this means, the blood test apparatus analyzes the components of the blood taken into the blood sensor.

Patent Document 1: Japanese Patent Application Laid-Open No. 2004-519302

DISCLOSURE OF INVENTION

Problems to be Resolved by the Invention

However, when a blood test is conducted using such conventional blood test apparatus, a patient has to move the blood sensor after puncturing. Therefore, after puncturing, the patient has to continue to touch the blood test apparatus with the skin of the finger from which blood is exuded for a while.

Here, since the patient cannot hold the blood test apparatus by his/her hand while the finger touches the blood test apparatus, the patient has to move the blood sensor in an unstable condition, so that the finger is likely to come off the blood test apparatus while the patient moves the blood sensor.

As a result of the above, a problem that a correct measurement can not be conducted occurs.

It is therefore an object of the invention is to provide a blood test apparatus that can reliably perform measurement from when the patient punctures his/her skin, to when a blood test is completed, without danger such that the finger comes off from the blood test apparatus and other places are stained with blood, and a blood test method using the blood test apparatus.

Means for Solving the Problem

A blood test apparatus according to the present invention punctures skin and analyzes a property of blood exuding from the skin. The blood test apparatus includes: blood sensors that each have an storing section for storing the blood exuding from the skin; a conveying unit that conveys a blood sensor from a first position to a second position where the blood is to be stored; a holding unit that holds the blood sensor in the second position; and a puncturing unit that punctures the skin while the blood sensor is held in the second position.

A cartridge according to the present invention is housed in a blood test apparatus that punctures skin and analyzes a property of blood exuding from the skin. The cartridge includes: a sensor chamber that stacks and stores blood sensors that each have an storing section for storing the blood; a conveying unit that conveys one blood sensor among the blood sensors stacked and stored in the sensor chamber, from a first position in the sensor chamber to a second position before puncturing is performed by the puncturing unit; and a holding unit that holds a blood sensor in the second position.

A cartridge according to the present invention is housed in a blood test apparatus that punctures skin and analyzes a property of blood exuding from the skin. The cartridge includes: a sensor chamber that stacks and stores blood sensors each having an storing section that stores the blood; a conveying unit that conveys one blood sensor among the blood sensors stacked and stored in the sensor chamber, from a first position in the sensor chamber to a second position before puncturing is performed by the puncturing unit; and a detected section that allows to externally detect a usage condition, a usage history and characteristic information of the blood sensors stacked and stored in the sensor chamber.

A cartridge according to the present invention is housed in a blood test apparatus that punctures skin and analyzes a property of blood exuding from the skin. The cartridge includes: a sensor chamber that stacks and stores blood sensors each having an storing section that stores the blood; a conveying unit that conveys one blood sensor among the blood sensors stacked and stored in the sensor chamber, from a first position in the sensor chamber to a second position before puncturing is performed by the puncturing unit; and a second holder on which the blood sensor is placed in the second position and that touches the skin.

A blood test method according to the present invention is for a blood test apparatus comprising a puncturing unit that punctures skin and a cartridge that stacks and stores blood sensors that each have an storing section that stores blood exuding from the skin. The method includes: conveying a blood sensor of the blood sensors stored in the cartridge, from a first position in the cartridge to a second position; puncturing the skin by the puncturing unit while the blood sensor is held in the second position; storing the blood exuding from the skin in the storing section of the blood sensor; and analyzing a component of the blood on the blood sensor.

Advantageous Effects of Invention

According to the present invention, a patient does not need to move blood sensors from when the skin is punctured to when the blood test is completed, so that the efficiency of a series of blood test operations, including puncturing, sampling blood and measurement, can be significantly improved, and also the reliability can be significantly improved.

Moreover, the finger is not likely to come off the blood test apparatus from when the patient punctures his/her skin to when the blood test is completed, so that the measurement can be reliably conducted, without danger such that other places are stained with blood.

BEST MODE FOR CARRYING OUT THE INVENTION

Hereinafter, embodiments of the present invention will be explained based on the accompanying drawings. Here, in description of each embodiment, directions such as top and bottom are defined, on the basis of the blood test apparatus in use.

Embodiment 1

Figure 1:
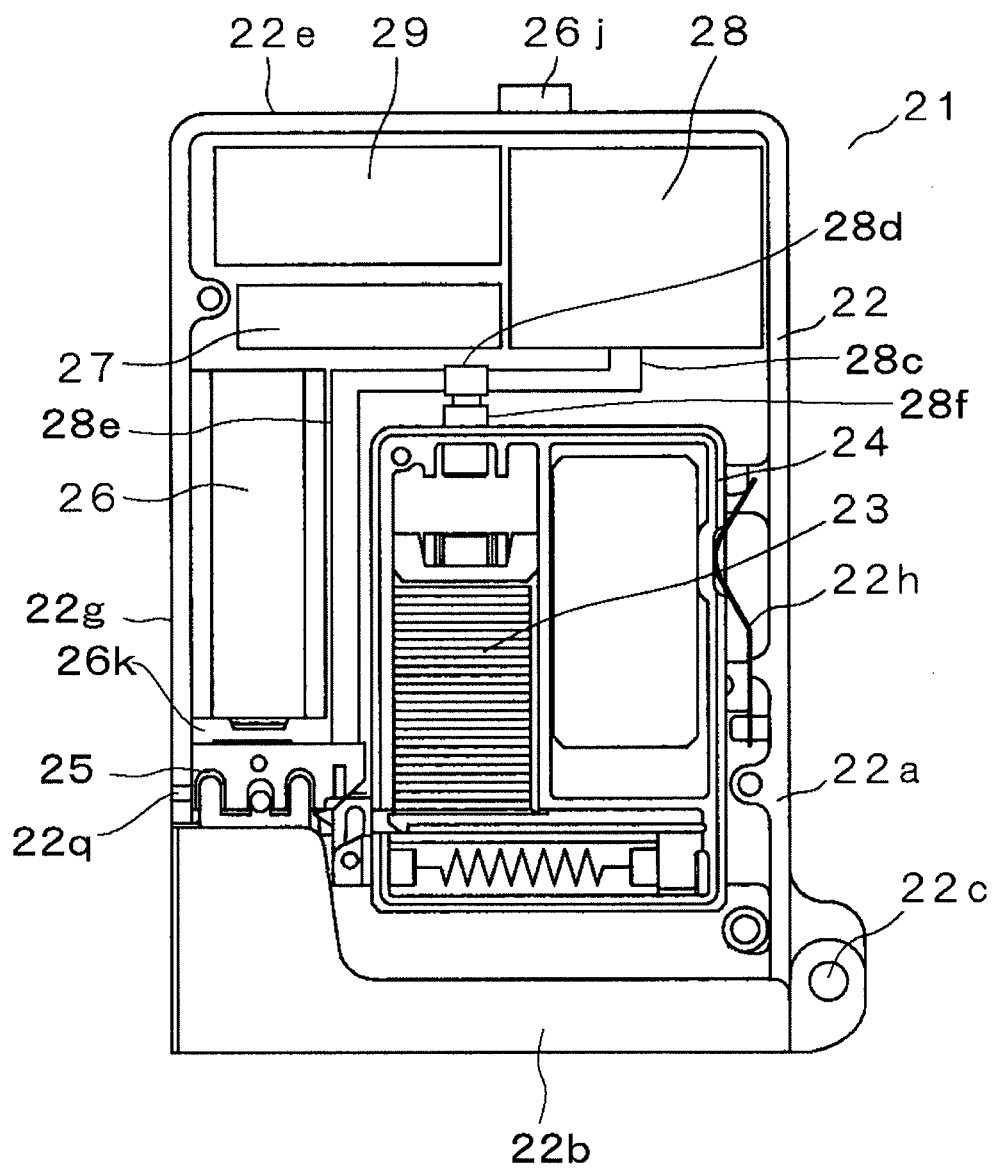
FIG. 1 is a cross sectional view of a blood test apparatus according to embodiment 1 of the present invention.
Figure 2:
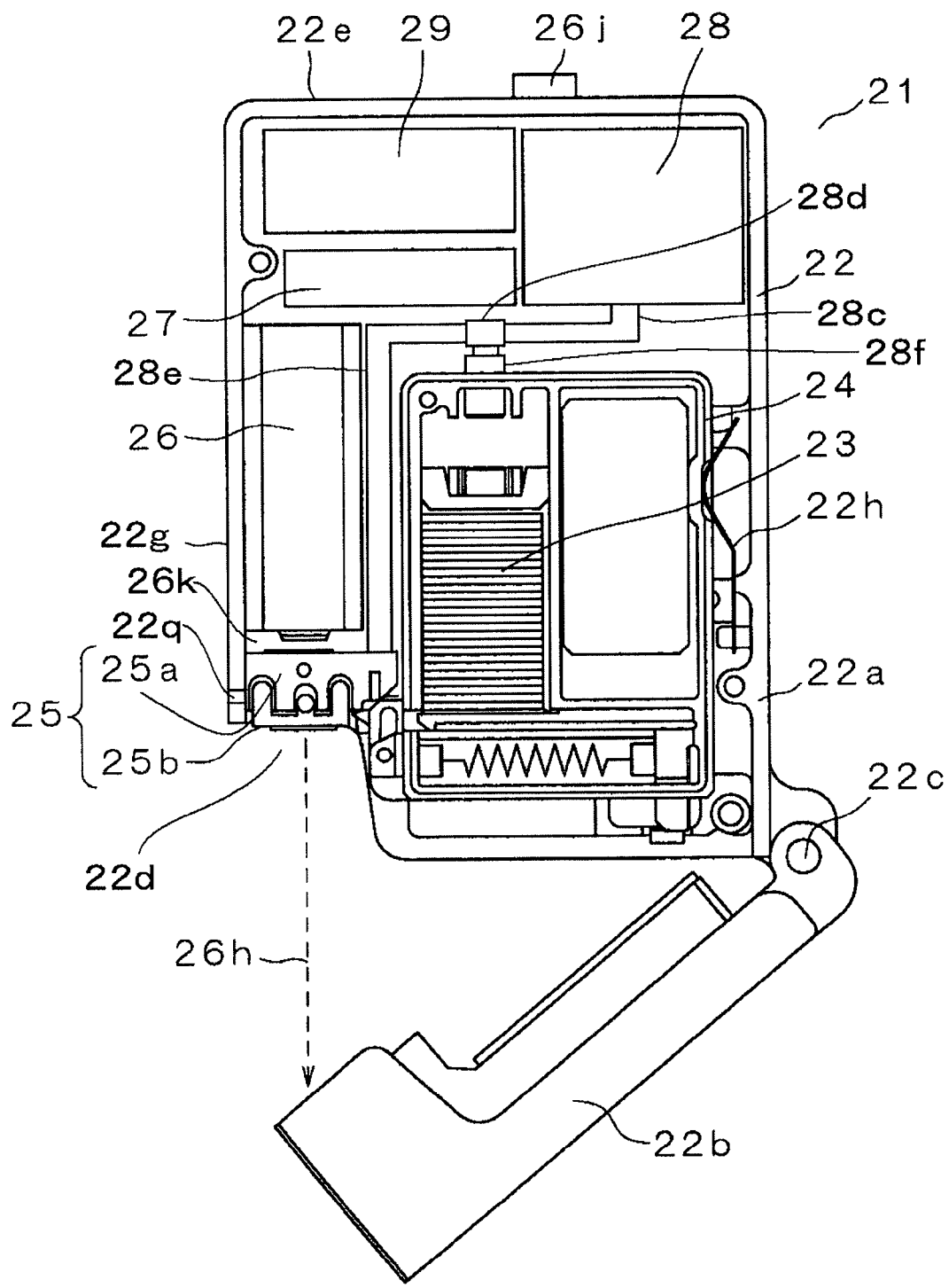
FIG. 2 is a cross sectional view of a blood test apparatus according to embodiment 1 of the present invention.
Figure 3:
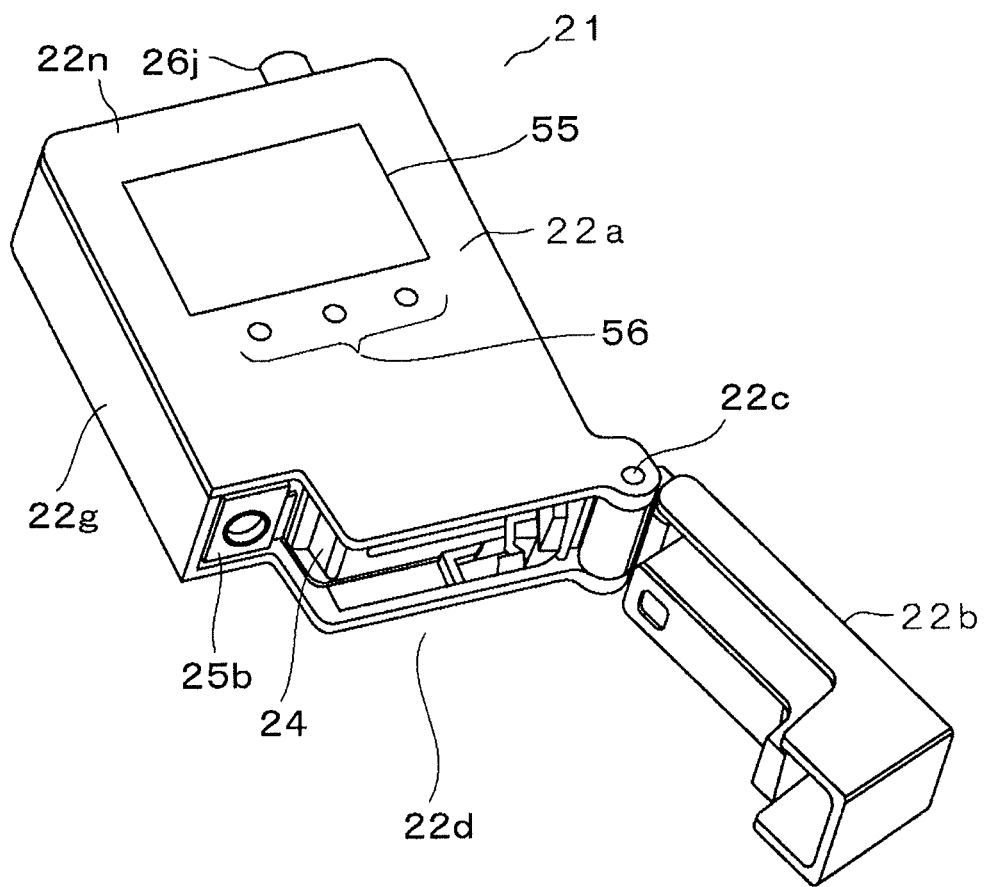
FIG. 3 is a perspective view of a blood test apparatus according to embodiment 1 of the present invention.
Figure 4:
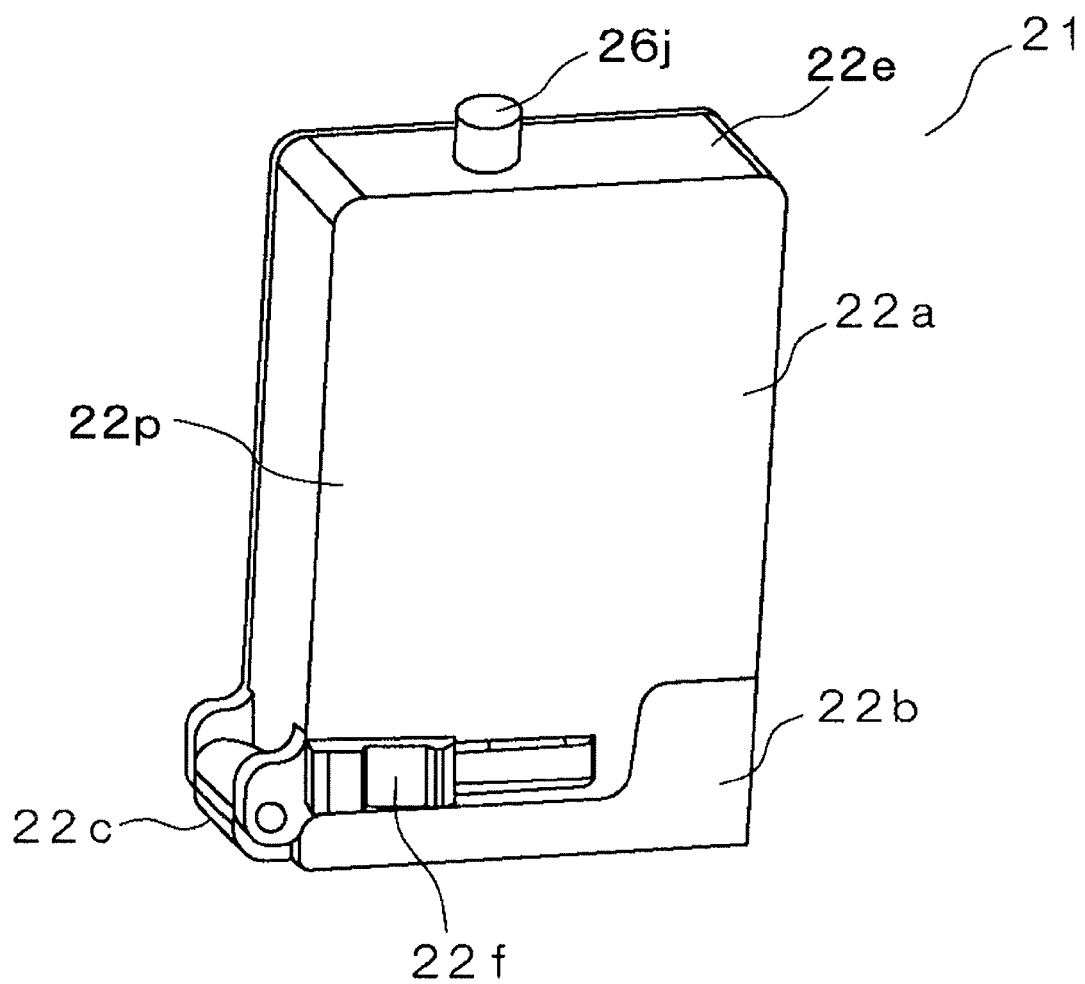
FIG. 4 is a perspective view showing the blood test apparatus from the rear according to embodiment 1 of the present invention.

FIGS. 1 and 2 are cross sectional views of blood test apparatus 21 according to the present embodiment. Here, in FIGS. 1 and 2, blood test apparatus 21 is shown in the direction in use, and the upward direction of each of FIGS. 1 and 2 means the upward direction of the blood test apparatus in use. FIG. 3 is a perspective view of blood test apparatus 21 according to the present embodiment. FIG. 4 is a perspective view showing blood test apparatus 21 from the rear.

As shown in FIGS. 1 and 2, the blood test apparatus 21 has housing 22, and housing 22 includes cartridge 24, holding section 25, laser emitting device 26, electrical circuit section 27, pump 28 and battery 29.

Housing 22 is made of for example, resin and has a substantially rectangular solid shape. Housing 22 includes main body 22a having opening 22d, and cover 22b for covering opening 22d. Cover 22b is pivotably coupled to main body 22a with a centrally-located spindle 22c. Cover 22b comes to rest when housing 22 is closed, that is, cover 22b covers opening 22d. In addition, cover 22b comes to rest in the first resting position where cover 22b is open about 30 degrees from main body 22a, and the second resting position where cover 22b is open about 90 degrees from main body 22a. FIG. 1 and FIG. 4 show a state where housing 22 is closed. In FIG. 2, cover 22b rests in the first resting position while housing 22 is open. FIG. 3 shows a state where cover 22b rests in the second resting position and housing 22 is open.

Cartridge 24 is removably mounted on main body 22a, and stacks and stores therein sensors 23. As shown in FIG. 3, cover 22b rests in the second resting position where the cover opens at the opening angle about 90 degrees, so that cartridge 24 can be easily replaced. In addition, sensors 23 stacked and stored in cartridge 24 are separated one by one and conveyed to holding section 25 by conveying unit. Here, the internal configuration of cartridge 24 will be described in detail later.

Holding section 25 is composed of first holder 25a provided above and second holder 25b provided below. Holding section 25 holds one sensor 23 which is separated and conveyed from cartridge 24 by sandwiching this sensor 23 between first holder 25a and second holder 25b.

Laser emitting device 26, which is one puncturing means is fixed on the position in the back of holding section 25 (the upward position in FIG. 3). Laser emitting device 26 emits laser light 26h to puncture the skin of a patient touching second holder 25b of holding section 25. Here, lens 26g for focusing light is disposed at the tip of laser emitting device 26 (see FIG. 21). Shield 26k, which is a lens protecting member, is replaceably mounted between lens 26g and first holder 25a. Shield 26k is made of glass and plastic allowing laser light to pass, and protects laser emitting device 26 and lens 26g from evaporated materials generated during puncturing with laser light.

When laser light 26h is emitted, cover 22b rests in the first resting position at the opening angle about 30 degrees as shown in FIG. 2, so that laser light 26h hits against a part of cover 22b and does not leak outside, thereby ensuring the safety.

Electrical circuit section 27 is electrically connected to sensors 23, puncturing button 26j, laser emitting device 26 and pump 28. Then, electrical circuit section 27 causes laser emitting device 26 to emit laser light 26h according to an electric signal indicating that puncturing button 26j is pushed. In addition, electrical circuit section 27 analyzes the components of the blood sampled on sensor 23. Moreover, electrical circuit section 27 causes pump 28 being a negative pressure means to generate a negative pressure at a predetermined timing.

Pump 28 applies a negative pressure to the inside of holding section 25 and cartridge 24. Pump 28 communicates with first holder 25a of holding section 25 through a first negative pressure path (passage 28c, valve 28d, and passage 28e). In addition, pump 28 communicates with cartridge 24 through a second negative pressure path (passage 28c, valve 28d, and passage 28f). Valve 28d has a function for switching between the first negative pressure path and the second negative pressure path.

When skin 10 touches holding section 25, applying a negative pressure to the inside of holding section 25 is started, and when the measurement is completed, applying the negative pressure is stopped. Then, when cover 22b is closed, applying a negative pressure to the inside of cartridge 24 is started, and after a certain time passes, applying the negative pressure is stopped. Otherwise, the negative pressure may be applied regularly into cartridge 24 at a predetermined time by means of a timer.

Battery 29 supplies electric power to laser emitting device 26, electrical circuit section 27 and pump 28.

Puncturing button 26j is provided on top face 22e of housing 22. When a patient depresses puncturing button 26j, an electric signal generated by the depression is output to electrical circuit section 27.

In addition, ejecting port 22q for ejecting sensor 23 which has been used is provided on side surface 22g of housing 22.

Positioning convex part 22h is provided inside housing 22. Positioning convex part 22h is formed by a leaf spring and is fitted in cartridge 24 to position cartridge 24.

Display section 55 and manual operation button 56 (see FIG. 3) are provided on front face 22n of housing 22. Display section 55 displays numerical values indicating a test result such as the property of blood (e.g. blood sugar level), and displays massages for informing about the current state or a warning. Operation button 56 operates for switching displays of display section 55, and setting and confirming registration data or a puncturing strength.

An operating lever 22f and slit hole 22m are provided on back face 22p of housing 22. Operating lever 22f is slidably engaged with slit hole 22m which is provided on the bottom of main body 22a. The patient slides operation lever 22f to move one sensor 23 from cartridge 24 to holding section 25. Here, when housing 22 is closed as shown in FIG. 4, operation lever 22f is locked.

Figure 5:
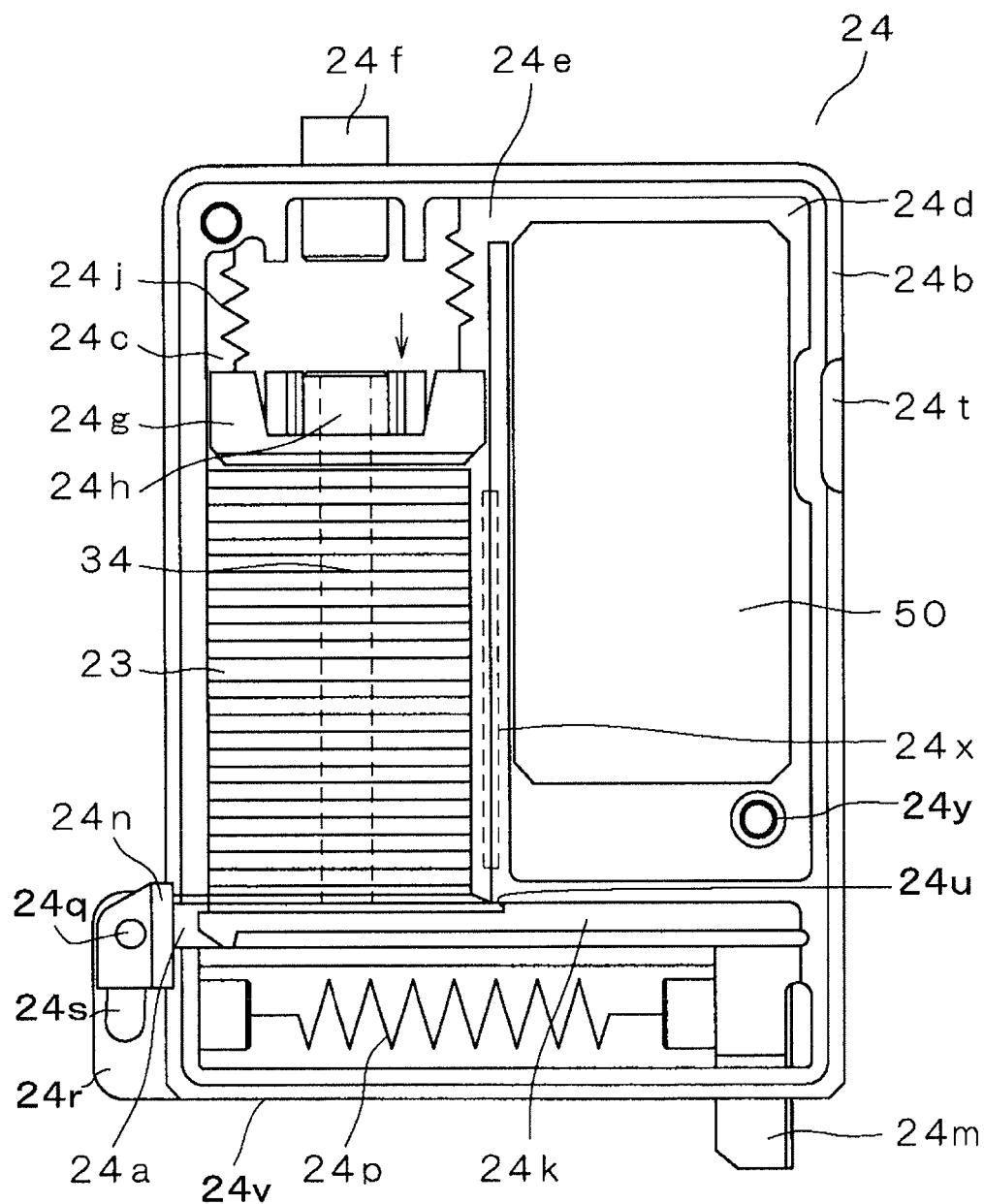
FIG. 5 is a cross sectional view of a cartridge according to embodiment 1 of the present invention.
Figure 6:
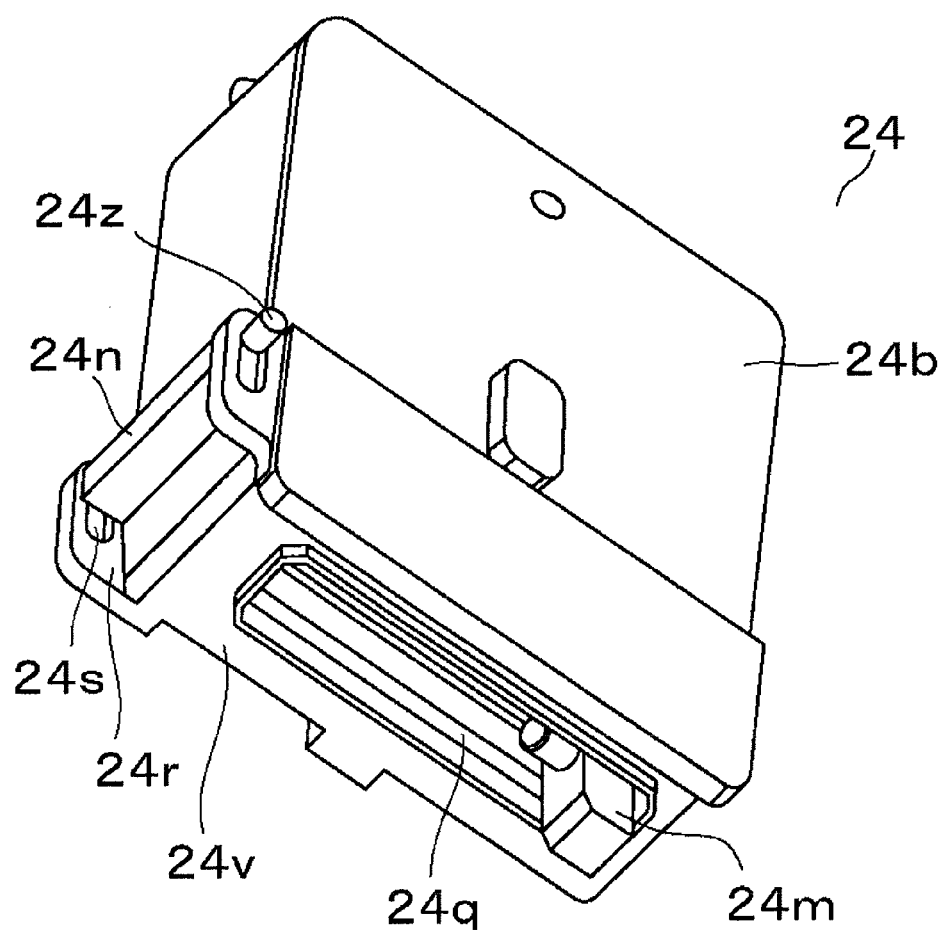
FIG. 6 is a perspective view showing the cartridge viewed from below according to embodiment 1 of the present invention.

Next, the internal configuration of cartridge 24 will be described in detail with reference to the drawings. FIG. 5 is a cross sectional view of cartridge 24. FIG. 6 is a perspective view showing cartridge 24 from below.

Case 24b is made of resin, for example and has a substantially rectangular solid shape. Positioning concave part 24t is provided on the side of case 24b. When cartridge 24 is inserted in main body 22a, positioning convex part 22h (see FIG. 1) of main body 22a is fitted into positioning concave part 24t to position cartridge 24.

Sensor chamber 24c and drying chamber 24d are provided in case 24b. Sensors 23 are stacked and stored in sensor chamber 24c. Desiccant 50 is stored in drying chamber 24. Sensor chamber 24c and drying chamber 24d are connected through passage 24e. Moreover, an air hole 24x may be provided on a contact surface between sensor chamber 24c and drying chamber 24d. By this means, sensor chamber 24c, in which sensors 23 are stacked and stored, can be dried through passage 24e or air hole 24x, so that the performance of each sensor 23 can be maintained.

Negative pressure outlet 24f formed above sensor chamber 24c has a cylindrical shape, and is connected to passage 28f that is a second negative pressure path, to apply a negative pressure to the inside of sensor chamber 24c. Spring 24j constituting a pressing section biases stacked and stored sensors 23 downward through pressure plate 24g also constituting a pressing section. Though-hole 24h communicating with storing section 34 of sensor 23 is provided at approximately the center of pressure plate 24g.

Consequently, the negative pressure guided from negative pressure outlet 24f to sensor chamber 24c can reduce the dampness in sensors 23 via though-hole 24h to maintain the performance of sensors 23.

Figure 7:
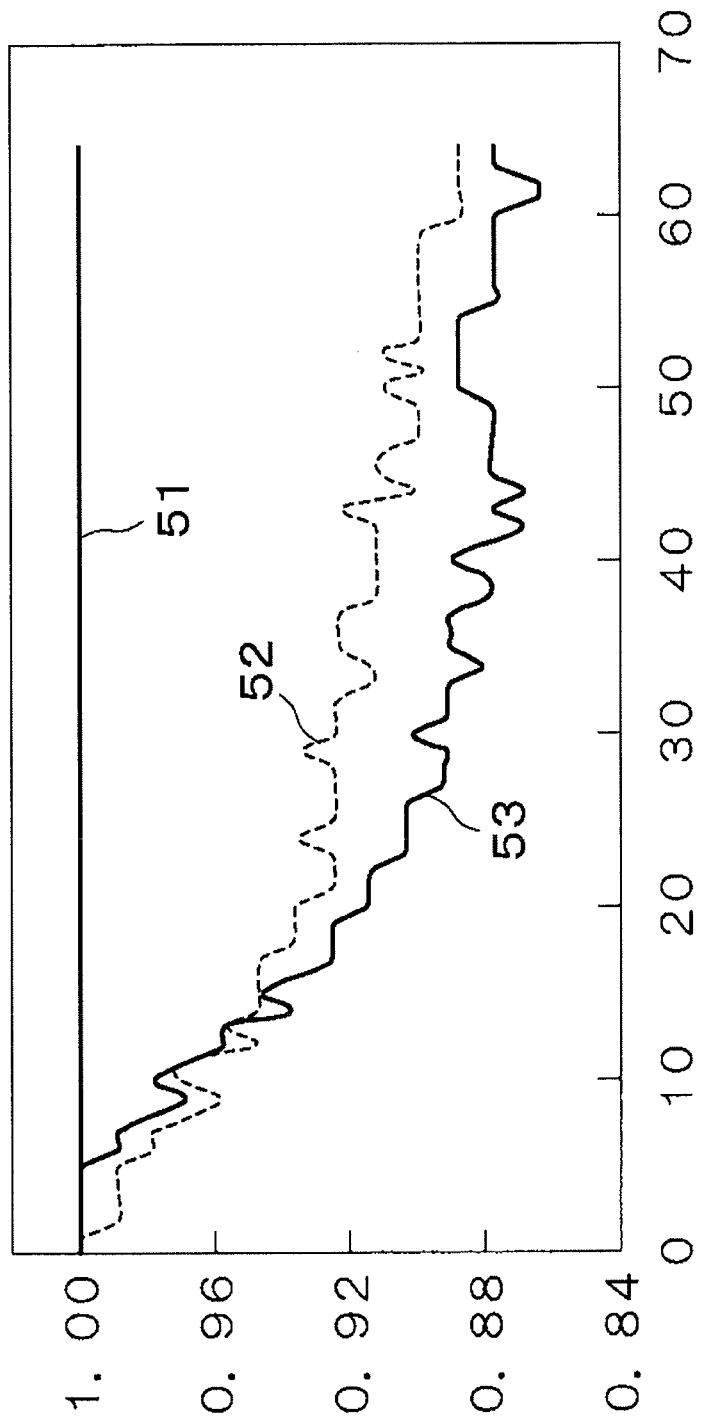
FIG. 7 is a characteristic view showing change in humidity (relative value) over time.

FIG. 7 is a characteristic view showing change in humidity (relative value) over time. The horizontal axis shows time (on the minute time scale), the vertical axis shows indexes (relative values) indicating relative ratios of the dampness in sensor chamber 24c, and straight line 51 indicates an instance where the dampness is "1", where there is no desiccant and no negative pressure. In addition, curved line 52 shows relative values between the dampness in case where there is not a desiccant but a negative pressure and the dampness in case where there is neither a desiccant nor a negative pressure. Moreover, curved line 53 shows relative values between the dampness in case where there is not a negative pressure but a desiccant and the dampness in case where there is neither a desiccant nor a negative pressure. Here, with respect to curved line 52, a negative pressure is applied for a certain time only once, and then the sensor chamber is left. Here, the capacity of sensor chamber 24 can stack and store 50 pieces of sensors 23.

As is clear from FIG. 7, similar effect may be achieved by both the instance when there is only a desiccant and the instance when there is only a negative pressure. That is, the similar effect can be made using a negative pressure, instead of desiccant 50 as before.

Thus, since the amount of desiccant 50 can be significantly reduced by reducing dampness using a negative pressure than ever before, so that cartridge 24 and blood test apparatus 21 can be compact and suitable for portable use, and the price can be reduced.

Here, as for an unused cartridge 24 in which desiccant 50 is stored, it is preferred that slit hole 24q, negative pressure outlet 24f and sensor outlet 24a are sealed to prevent from being affected by outside dampness. Alternatively, the whole of unused cartridge 24 may be stored in a sealed container to obtain substantially the same effect. Moreover, a cylindrical tube having the outer diameter that is smaller than the inner diameter of negative pressure outlet 24f may be provided such that the cylindrical tube faces negative pressure outlet 24f, so that the sealing onto negative pressure outlet 24f can be easily broken through only by mounting cartridge 24 in main body 22a.

Pressure sensor 24y is mounted on drying chamber 24d. Pressure sensor 24y measures the degree of negative pressure in drying chamber 24d. Based on the measurement result of pressure sensor 24y, the negative pressure in sensor chamber 24c and drying chamber 24d can be appropriately controlled through negative pressure outlet 24f such that the negative pressure is not more than a predetermined value, therefore sensors 23 can be always dry.

A conveying unit is formed below sensor chamber 24c composed of slider plate 24k, arm 24m and spring 24p. Slider plate 24k has flat plate shape and includes cutout step 24u for conveying one sensor 23. Arm 24m is fixed to slider plate 24k and projects from slit hole 24q formed on an under surface 24v of cartridge 24. In addition, arm 24m abuts on pressure plate 22k (see FIG. 10) coupled to operation lever 22f (see FIG. 4) that is provided in main body 22a. Arm 24m slides in slit hole 24q to move slider plate 24k and arm 24m. Spring 24q biases slider plate 24k and arm 24m in a direction opposite to sensor outlet 24a.

Moreover, shutter 24n for opening and closing sensor outlet 24a is provided in cartridge 24. Pin 24z of shutter 24n slides in guide hole 24s of rib 24r provided on case 24b, so that shutter 24n moves up and down. Sensor outlet 24a closes when shutter 24n is located on the upper end, conversely sensor outlet 24a opens when shutter 24n is located on the bottom end.

Figure 8:
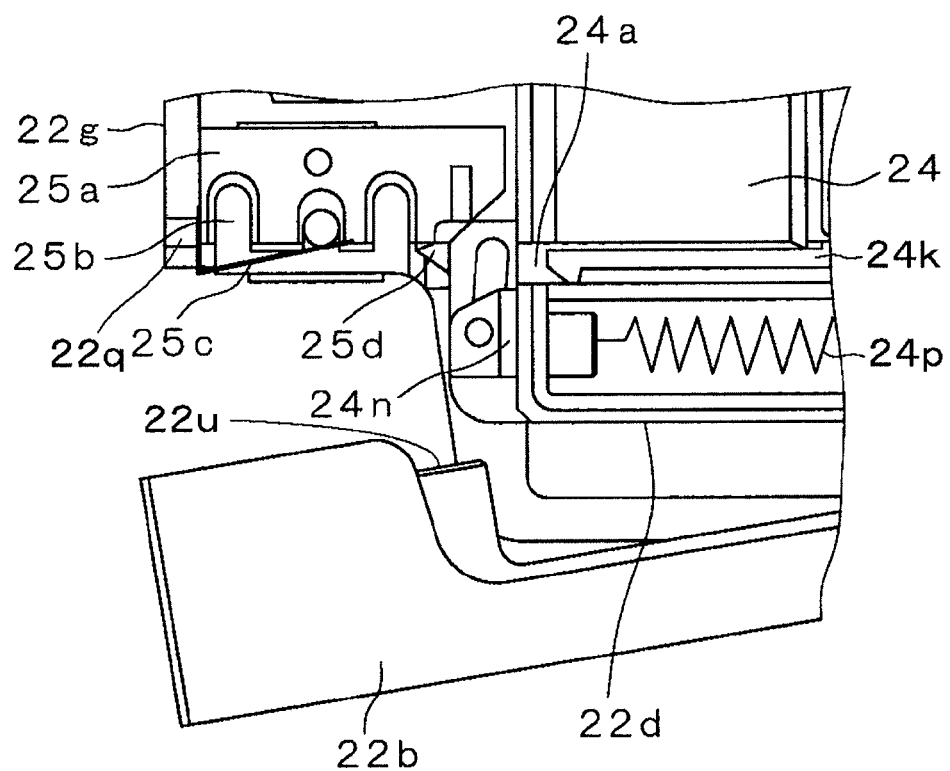
FIG. 8 is a cross sectional view of a holding section of the blood test apparatus and its nearby primary parts according to embodiment 1 of the present invention.
Figure 10:
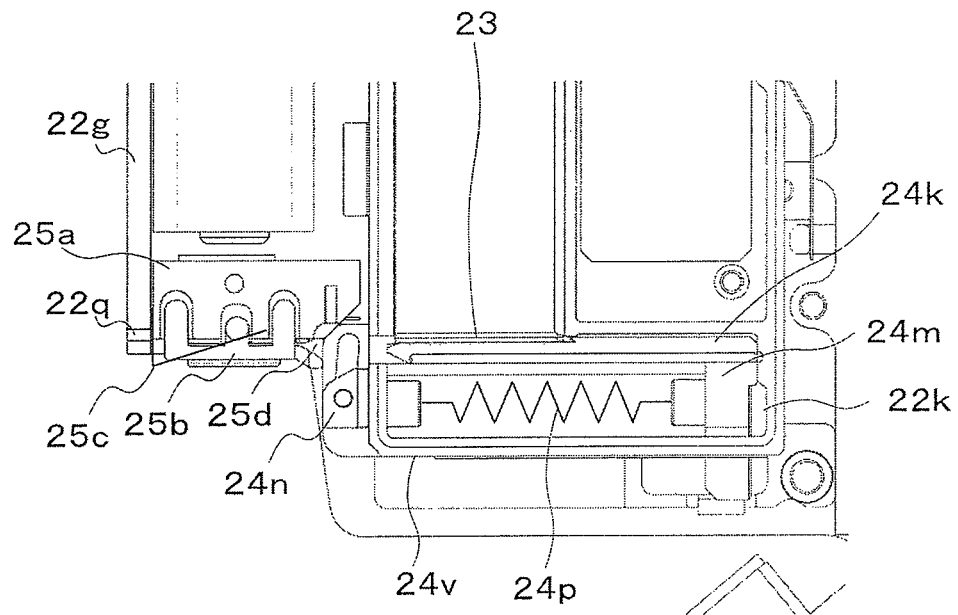
FIG. 10 is a cross sectional view of the holding section of the blood test apparatus and its nearby primary parts according to embodiment 1 of the present invention.
Figure 11:
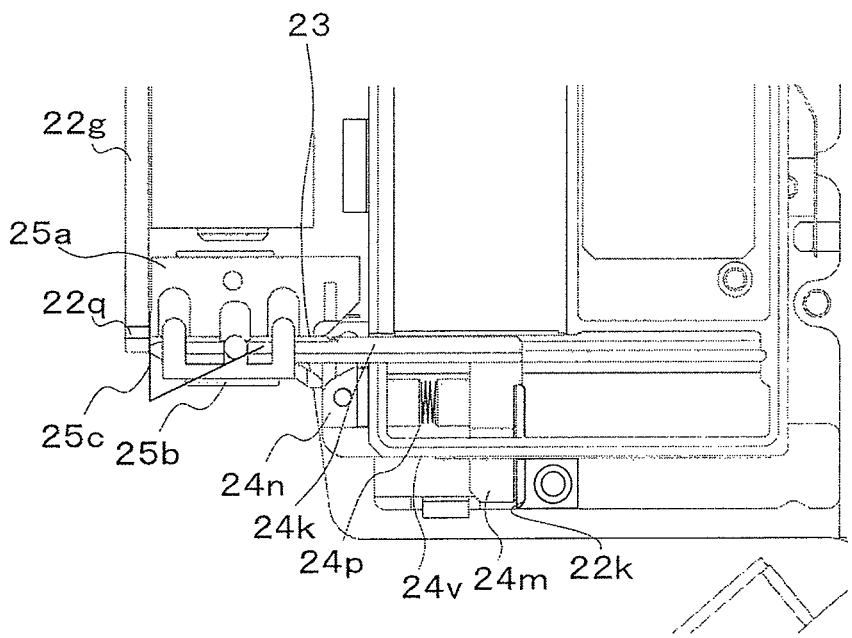
FIG. 11 is a cross sectional view of the holding section of the blood test apparatus and its nearby primary parts according to embodiment 1 of the present invention.
Figure 12:
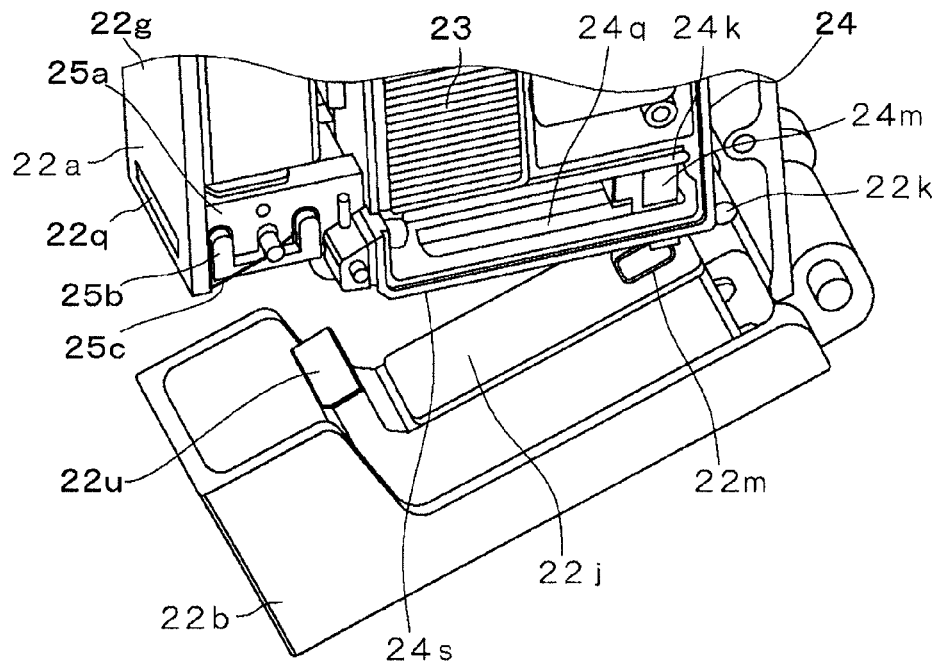
FIG. 12 is a perspective view of the holding section of the blood test apparatus and its nearby primary parts according to embodiment 1 of the present invention.

FIG. 8, FIG. 9, FIG. 10, and FIG. 11 are cross sectional views showing holding section 25 and its nearby primary parts. FIG. 12 is a perspective view showing holding section 25 and its nearby primary parts. Here, FIG. 8 shows a state such that closed housing 22 is opening by moving cover 22b to the first resting position.

Figure 9:
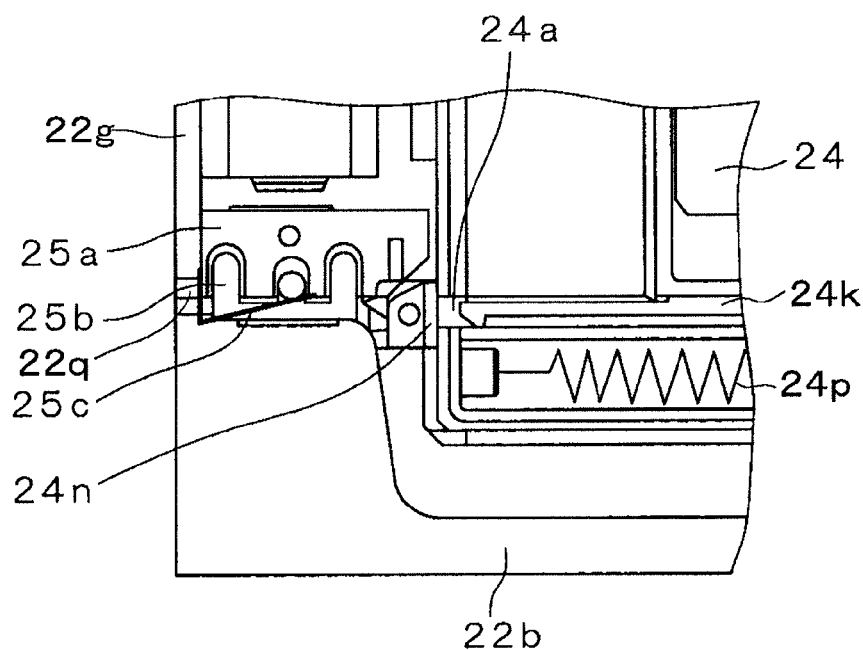
FIG. 9 is a cross sectional view of the holding section of the blood test apparatus and its nearby primary parts according to embodiment 1 of the present invention.

FIG. 9 shows a state where housing 22 is closed. FIG. 10, FIG. 11 and FIG. 12 show a state in which cover 22b rests in the first resting position. In addition, FIG. 10 and FIG. 12 show a state before sensors 23 is inserted in holding section 25. FIG. 11 shows a state when sensors 23 are inserted in holding section 25.

First holder 25a is fixed to housing 22. Second holder 25b is engaged with the first holder at one end thereof, and is biased toward first holder 25a by leaf spring 25c. Opening 25d is formed on the boundary between first holder 25a and second holder 25b. Opening 25d is provided in a position facing sensor outlet 24a. That is, the surfaces of first holder 25a and second holder 25b sandwiching sensor 23 are positioned on the track on which sensors 23 are conveyed by slider plate 24k. Here, according to the present invention, first holder 25a may be movable and second holder 25b is fixed to the housing. In this case, first holder 25a will be biased toward second holder 25b by leaf spring 25c.

Sensor outlet 24a of cartridge 24 opens and closes in conjunction with rotating cover 22b. That is, as shown in FIG. 8, when cover 22b rotates to open housing 22, shutter 24n is lowered by gravitation to open sensor outlet 24a. At this time, the patient slides operation lever 22f toward holding section 25, so that slider plate 24k and arm 24m are pushed by pressure plate 22k and move toward sensor outlet 24a as shown in FIG. 10, FIG. 11 and FIG. 12. At this time, one sensor 23, which is the bottommost sensor among stacked and stored sensors 23 on slider plate 24k, is conveyed from sensor outlet 24a to holding section 25.

Sensor 23 conveyed from sensor outlet 24a of cartridge 24 is inserted between first holder 25a and second holder 25b, from opening 25d of holding section 25, against the elasticity of leaf spring 25c, and is fixed by the pressing force by the elasticity of leaf spring 25c. Here, used sensor 23 is pushed by an unused sensor 23 which is newly inserted, and is ejected from ejecting port 22q provided on main body 22a.

Since sensor 23 is fixed between first holder 25a and second holder 25b, the distance between laser emitting device 26 and the lower side of holder 25b is held constant. Consequently, laser light 26h can always focus on a fixed position near the surface of skin.

When the patient releases operation lever 22f from his/her hand, slider plate 24k automatically returns to the inside of case 24b because of being biased by spring 24p. Accordingly, battery is not consumed. Here, such conveying operation may be electrically performed using a motor and so forth.

As shown in FIG. 9 and FIG. 12, when cover 22b is rotated to close housing 22, shutter 24n is pushed up by pressing surface 22u (see FIG. 8) provided on cover 22b, so that sensor outlet 24a closes. By this means, sensor 23 cannot be conveyed from cartridge 24 to holding section 25. In addition, when cover 22b is closed, slit hole 24q is sealed by pressing section 22j provided on cover 22b. Consequently, the inside of cartridge 24 becomes in a sealed-up state. Here, such sealed-up state can be achieved by attaching an elastic material on the surface of pressing section 22j to which at least slit hole 24q is attached.

When housing 22 is closed, pressure plate 22k and arm 24m are fitted into fitting hole 22m provided on pressing section 22j. Consequently, operation lever 22f (see FIG. 4), pressure plate 22k, slider plate 24k and arm 24m are locked.

Here, although an instance where sensor outlet 24a of cartridge 24 opens and closes in conjunction with the rotation of cover 22b has been described, the present invention is not limited to this regard, and, independent of the rotation of cover 22b, sensor outlet 24 of cartridge 24 may be opened by being pressed by slider plate 24k and automatically close because of being biased by a spring and so forth when slider plate 24k returns to the inside of case 24b.

Figure 13:
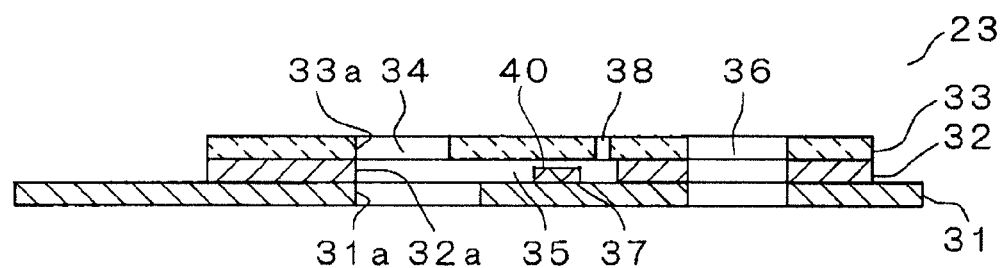
FIG. 13 is a cross sectional view of a sensor according to embodiment 1 of the present invention.

FIG. 13 is a cross sectional view of sensors 23 stacked and stored in cartridge 24. Sensor 23 has a flat rectangular shape and is composed of substrate 31, spacer 32 that is pasted on the upper surface of substrate 31, and cover 33 that is pasted on the upper surface of spacer 32.

Sensor 23 includes storing section 34 for storing blood. Storing section 34 is provided in a position where laser light 26h passes when sensor 23 is mounted in holding section 25. Storing section 34 is a space composed of substrate hole 31a formed on substrate 31, spacer hole 32a formed on spacer 32 and cover hole 33a formed on cover 33.

Supply path 35 for supplying blood 11 is coupled to storing section 34 at one end thereof, and guides blood 11 stored in storing section 34 to detecting section 37 by utilizing capillary action. The other end of supply path 35 is coupled to an air hole 38. Here the capacity of storing section 34 is about 1 µL, and the capacity of supply path 35 is about 0.15 µL. Thus, it is possible to test using a small amount of blood 11, so that the burden on the patient can be reduced.

Positioning hole 36 is provided by penetrating sensor 23 and determines the mounting position of sensor 23. Detecting section 37 measures the blood sugar level and so forth of blood 11.

Reagent 40 is arranged on detecting section 37. This reagent 40 can be obtained by adding and dissolving PQQ-GDH (0.1 to 5.0 U/sensor), potassium ferricyanide (10 to 200 millimole), maltitol (1 to 50 millimole) and taurine (20 to 200 millimole) in a CMC solution of 0.01 to 2.0 wt % to prepare a reagent solution, by dropping the reagent solution on detecting section 37 formed on substrate 31 and drying. This reagent 40 is progressively degraded due to moisture absorbent.

Here, an electrically conductive layer is formed on the upper surface of substrate 31 by the sputtering method or the vapor deposition method using materials such as gold, platinum, or palladium. Detection electrodes 41 to 45 (see FIG. 14A and FIG. 14B), connection electrodes 41a to 45a derived from these detection electrodes 41 to 45 and identification electrode 47a (as shown in FIG. 14B) are integrally formed by applying laser machining to the electrically conductive layer. Polyethylene terephthalate (PET) is used for the material of substrate 31, spacer 32 and cover 33. The material is used common to these components in this way, so that the management cost can be reduced.

Figure 14A:
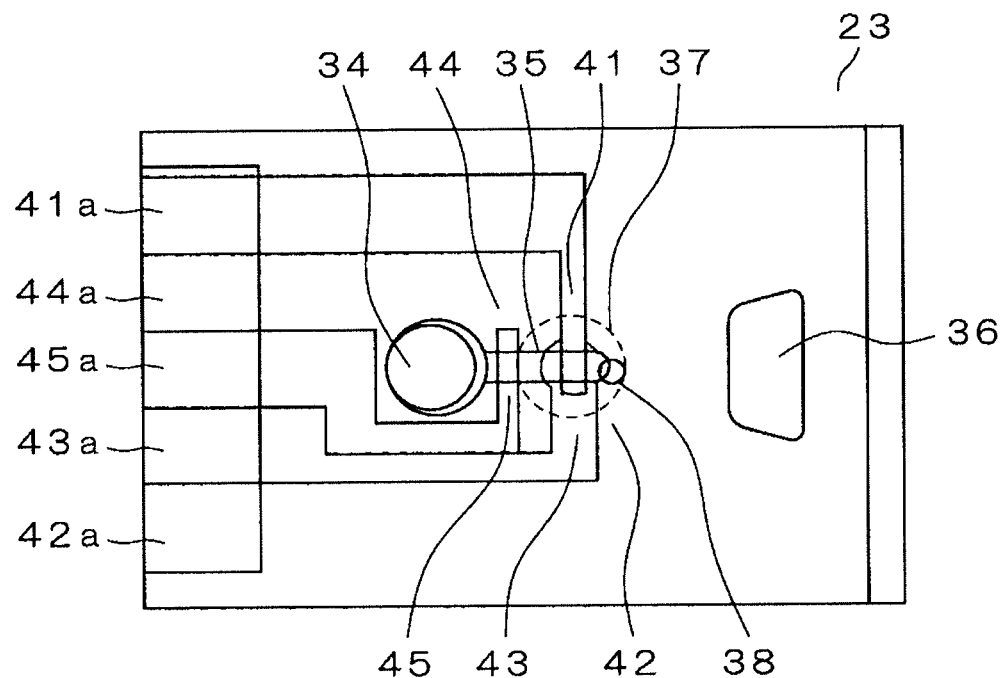
FIG. 14A is a plan view of a sensor according to embodiment 1 of the present invention.
Figure 14B:
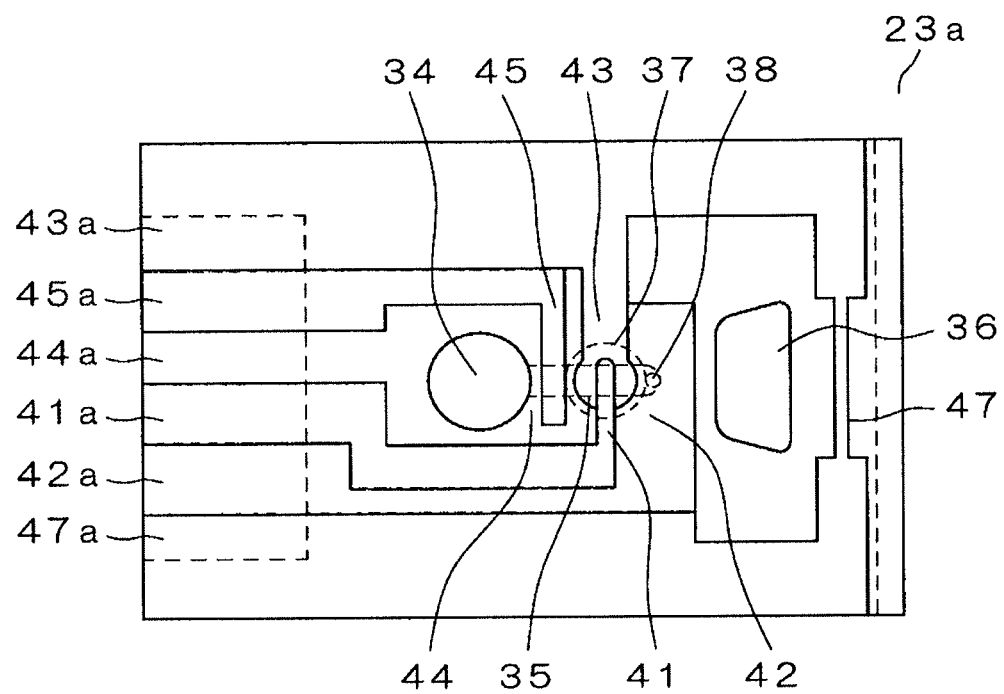
FIG. 14B is a plan view of a sensor according to embodiment 1 of the present invention.
Figure 15A:
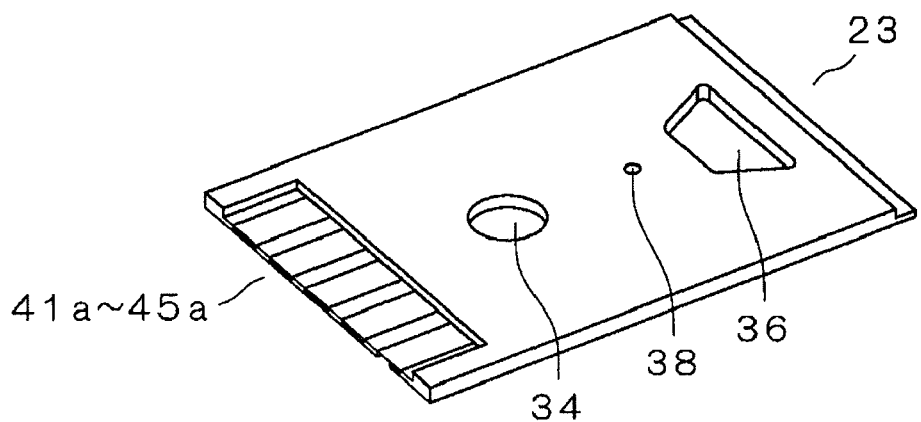
FIG. 15A is a perspective view of a sensor according to embodiment 1 of the present invention.
Figure 15B:
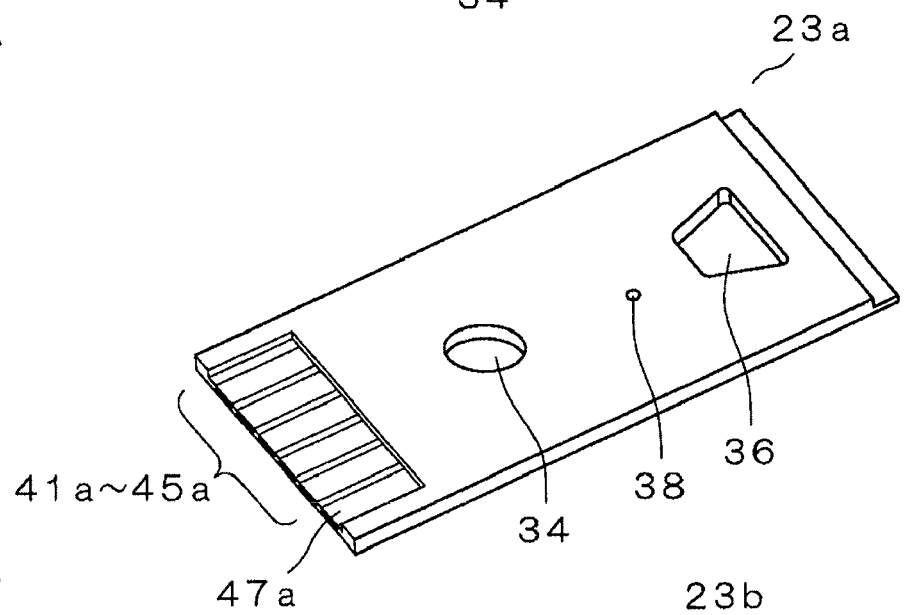
FIG. 15B is a perspective view of a sensor according to embodiment 1 of the present invention.
Figure 15C:
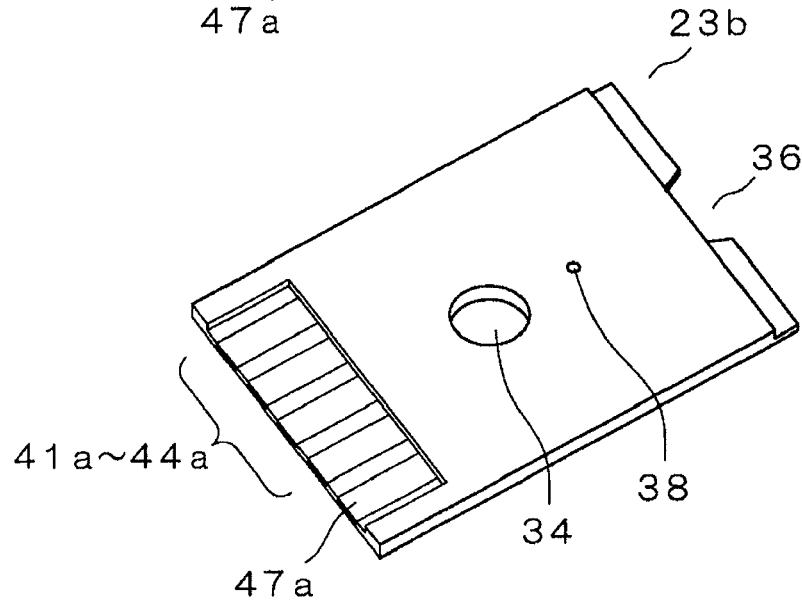
FIG. 15C is a perspective view of a sensor according to embodiment 1 of the present invention.

FIG. 14 is a plane view of sensor 23, and FIG. 15 is a perspective view of sensor 23. FIG. 14 A and FIG. 15 A show sensor 23 having 5 electrodes not including identification electrode 47a, and FIG. 14B and FIG. 15B show sensor 23 having 6 electrodes including identification electrode 47a. In addition, FIG. 15 C shows an instance where the shape of positioning section 36 is different from that of FIG. 15A and FIG. 15B.

Now, sensor 23 will be described with reference to FIGS. 14 B and 15 B with 6 electrodes.

Storing section 34 is formed approximately at the center of plate-like sensor 23, connection electrodes 41a to 45a and identification electrode 47a are formed on one end of sensor 23, and positioning section 36 is formed on the other end of sensor 23. Positioning section 36 is a hole, and has a trapezoidal shape narrowing toward storing section 34. Air hole 38 is formed between positioning section 36 and storing section 34.

Storing section 34, detection electrode 44, detection electrode 45, again detection electrode 44, detection electrode 43, detection electrode 41, again detection electrode 43 and detection electrode 42 are provided on supply path 35, in the order described.

In addition, reagent 40 (see FIG. 13) is placed on detection electrodes 41 and 43. Identifying section 47 formed by a conductor pattern is formed between detection electrode 43 and identification electrode 47a.

Blood test apparatus 21 (see FIG. 2) detects whether there is electrical conduction between connection electrode 43a and identification electrode 47a to identify whether sensor 23 is mounted in holding section 25. Here, in case where there is not electrical conduction when sensor 23 is conveyed to holding section 25, blood test apparatus 21 displays on display section 55 (see FIG. 22) a warning indicating that sensor 23 is not mounted in holding section 25.

By changing the electric resistance of identifying section 47, it is possible to store information of the calibration curve and also store manufacturing information. Therefore, a blood test can be more accurately performed by using those information.

Here, although FIG. 14A shows an instance where sensor 23 has 5 electrodes composed of all detection electrodes not including identification electrode 47a, it is possible to assign an identification electrode instead of one of the detection electrodes to have 5 electrodes. In this case, the automatic identification by the electrode can be performed as with an instance having 6 electrodes as shown in FIG. 14B.

In addition, while sensor 23 shown in FIG. 14 and FIG. 15 is formed of a rectangular plate-like body, the shape of sensor 23 is not limited in the present invention. For example, the shape of sensor 23 may be a square and a polygon other than a quadrangle, or a semicircle.

Moreover, the shape of positioning section 36 is not limited in the present invention, for example, positioning section 36 may be a hole having a shape such as a quadrangle, a polygon other than a quadrangle, a semicircle, a circle or an oval. Still more, positioning section 36 may not be hole but may be concave part.

Figure 16:
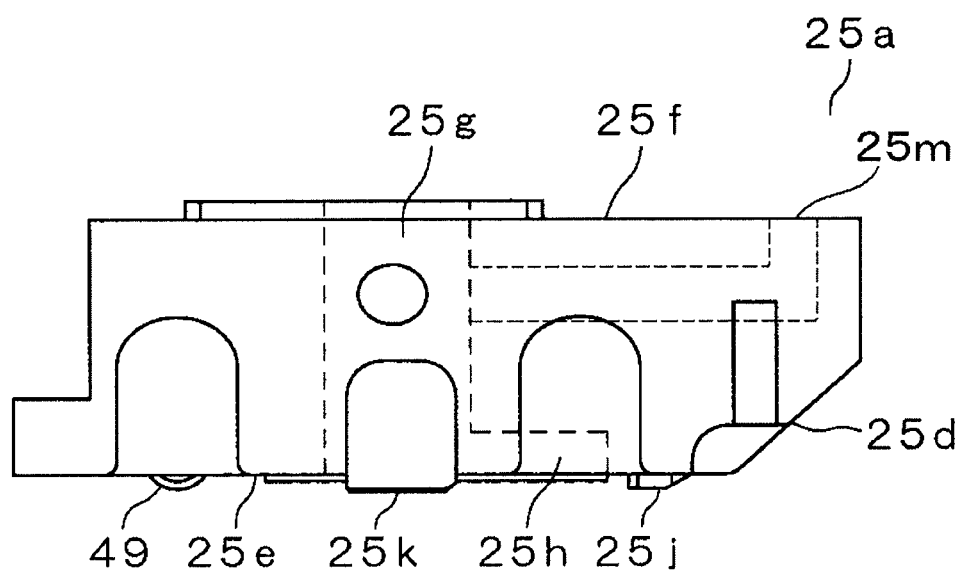
FIG. 16 is a side view of a first holder of the blood test apparatus according to embodiment 1 of the present invention.

FIG. 16 is a side view of first holder 25a constituting holding section 25. FIG. 17 is an external perspective view of first holder 25a viewed from under surface 25e.

Figure 17A:
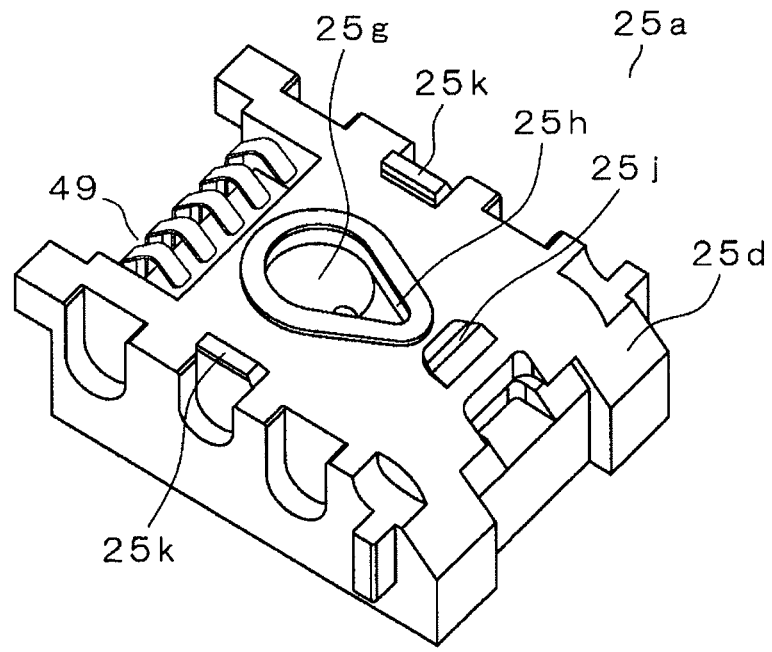
FIG. 17A is an external perspective view of the first holder of the blood test apparatus according to embodiment 1 of the present invention.
Figure 17B:
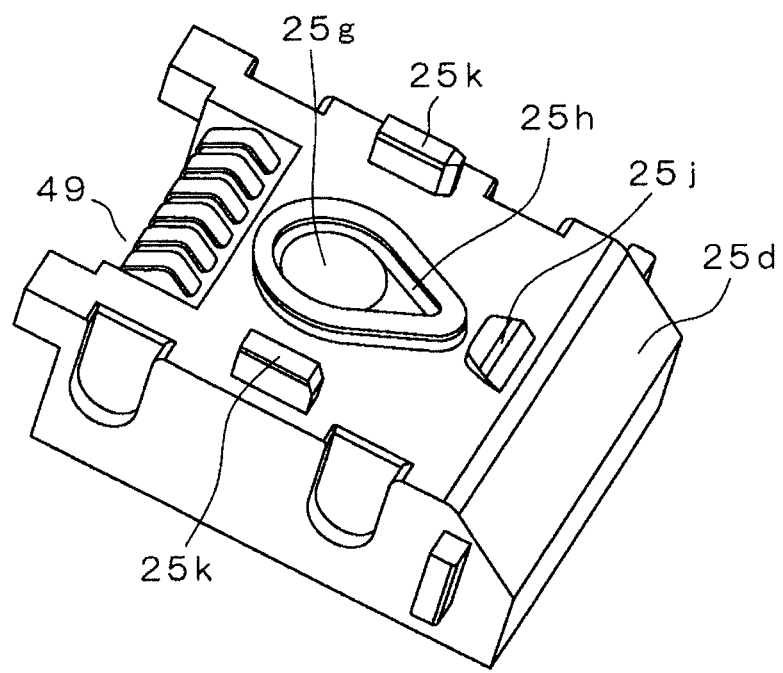
FIG. 17B is an external perspective view of the first holder of the blood test apparatus according to embodiment 1 of the present invention.

FIG. 17A shows an instance where sensor 23 has 5 electrodes, and FIG. 17B shows an instance where sensor 23 has 6 electrodes. FIG. 17A is the same as FIG. 17 B except the number of connectors 49 is different from each other. Now first holder 25a will be described with reference to FIG. 16 and FIG. 17B with 6 electrodes.

First holder 25a is provided with a hole 25g penetrating from top surface 25f to bottom surface 25e in a position through which puncturing laser light 26h (see FIG. 2) passes. Here, when a needle puncturing device is used instead of laser emitting device 26, a puncture needle passes through this hole 25g.

In addition, notch part 25h is provided on the lower part of hole 25g in order to assure the effect of capillary action through supply path 35 formed on sensor 23. Negative pressure is supplied through this hole 25g. Here, hole 25m in communication with this hole 25g is provided on second holder 25b.

Side hole 25n is provided on the side surface of hole 25g, for ejecting the evaporated material produced by the puncture with laser light 26h by the operation of pump 28 (see FIG. 2).

Projection 25j is provided between opening 25d and hole 25g. Projection 25j is engaged with positioning section 36 provided on sensor 23. Projection 25j has a trapezoidal shape narrowing toward hole 25g. The thickness of projection 25j gradually increases from opening 25d to hole 25g. Consequently, inserted into holding section 25, sensor 23 is easily fixed in holding section 25.

Two convex parts 25k are provided on both sides of first holder 25a, just beside hole 25g. The distance between the inner surfaces of two convex parts 25k may be slightly wider than the width of sensor 23. Connectors 49 are provided in the opposite position of opening 25d. Connectors 49 are in contact with connection electrodes 41a to 45a and identification electrode 47a, and are connected to electrical circuit section 27. Here, projection 25j and convex parts 25k may be provided on second holder 25b (see FIG. 8 for example).

Figure 18:
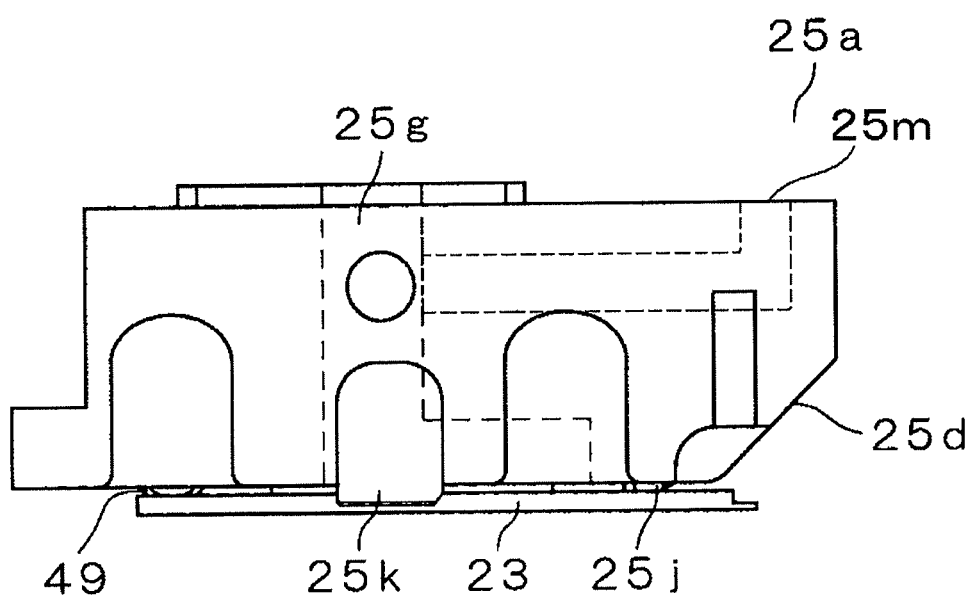
FIG. 18 is a side view of the first holder of the blood test apparatus according to embodiment 1 of the present invention.
Figure 19A:
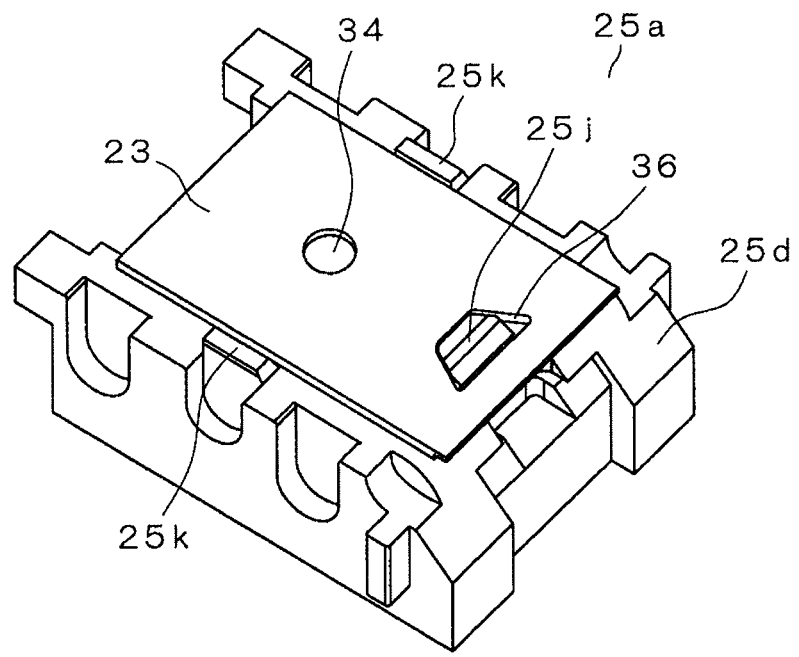
FIG. 19A is a perspective view of the first holder of the blood test apparatus according to embodiment 1 of the present invention.
Figure 19B:
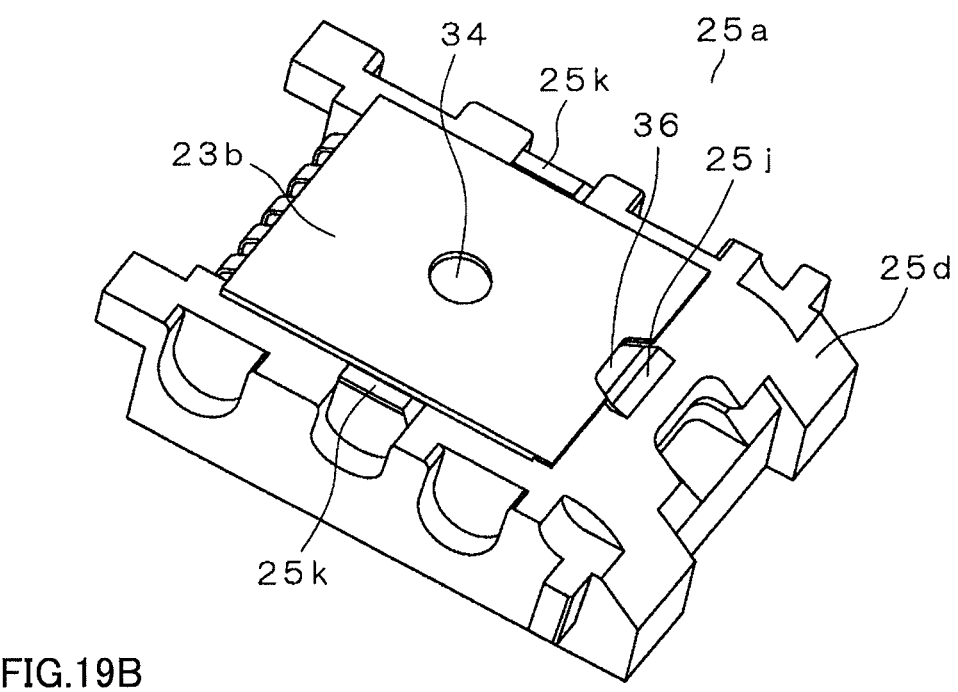
FIG. 19B is a perspective view of the first holder of the blood test apparatus according to embodiment 1 of the present invention.

FIG. 18 is a side view of first holder 25a in a state where sensor 23 is mounted. FIG. 19 is a perspective view of first holder 25a from bottom, where sensor 23 is mounted. Here, FIG. 19A shows an instance where sensor 23 having hole-shaped positioning section 36 (see FIG. 15A and FIG. 15B) is mounted on first holder 25a, and FIG. 19B shows an instance where sensor 23b having concave-shaped positioning section 36 (see FIG. 15C) is mounted on first holder 25a.

As shown in FIG. 18 and FIG. 19, sensor 23 is positioned in the horizontal direction, by engaging positioning section 36 with projection 25j and by defining between convex parts 25k. In this state, storing section 34 formed in sensor 23 communicates with hole 25g (see FIG. 17 and FIG. 17B). At this time, connector 49 is in contact with connection electrodes 41a to 45a and identification electrode 47a which are formed on sensor 23.

Figure 20:
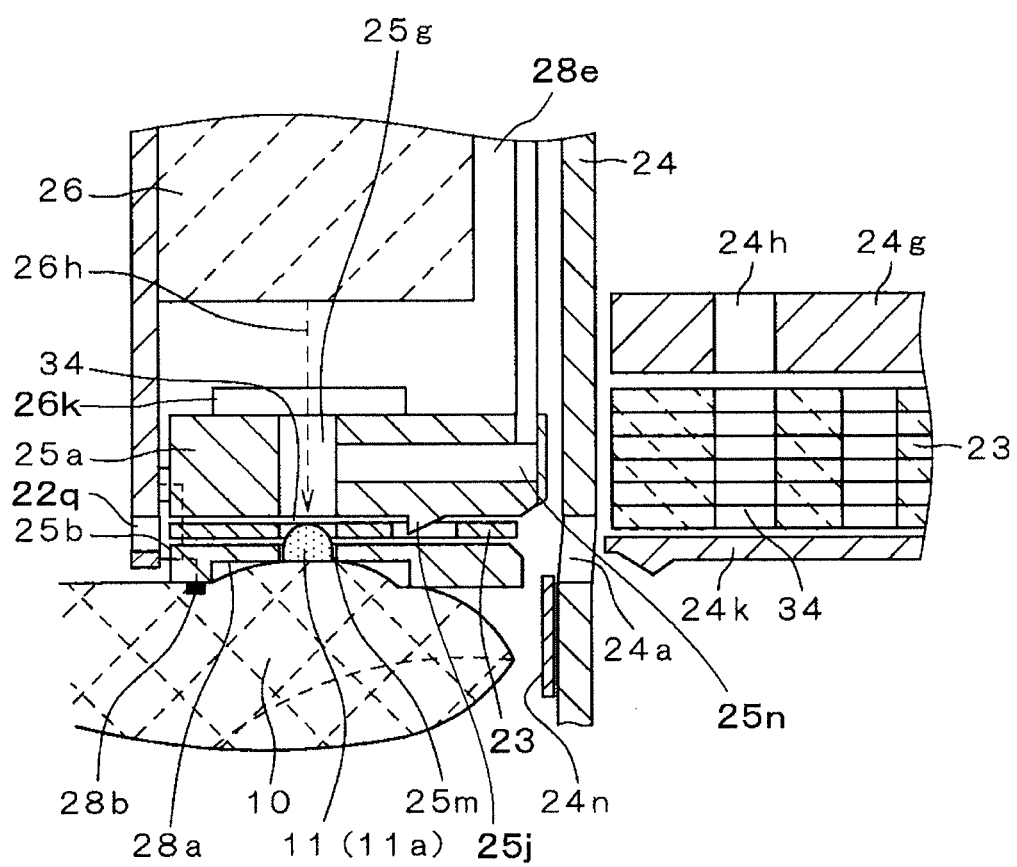
FIG. 20 is a cross sectional view of the holding section of the blood test apparatus and its nearby primary parts according to embodiment 1 of the present invention.

FIG. 20 is a cross sectional view showing holding section 25 and its nearby primary parts in a measuring operation using blood test apparatus 21. As shown in FIG. 20, negative pressure chamber 28a is formed by the surface of skin 10 and the under surface of second holder 25b. Negative pressure chamber 28a is connected to pump 28 (see FIG. 1) through hole 25m formed on second holder 25b, hole 25g of storing section 34 and first holder 25a, side hole 25n and passage 28e. Skin detecting sensor 28b is provided on the convex part forming the periphery of negative pressure chamber 28a. Skin detecting sensor 28b detects whether skin 10 is in contact with the under surface of second holder 25b.

Laser light 26h emitted from laser emitting device 26 passes straight through hole 25g of first holder 25a, storing section 34 of sensor 23 and hole 25m of second holder 25b, and punctures skin 10. When skin 10 is punctured, blood 11 exudes from skin 10 and forms blood droplet 11a.

In addition, the evaporated material produced by the puncture with laser light 26h is ejected through side hole 25n and passage 28e for negative pressure by the operation of pump 28.

Therefore, little stain and dust adhere to lens protect member 26k provided above hole 25g.

Figure 21:
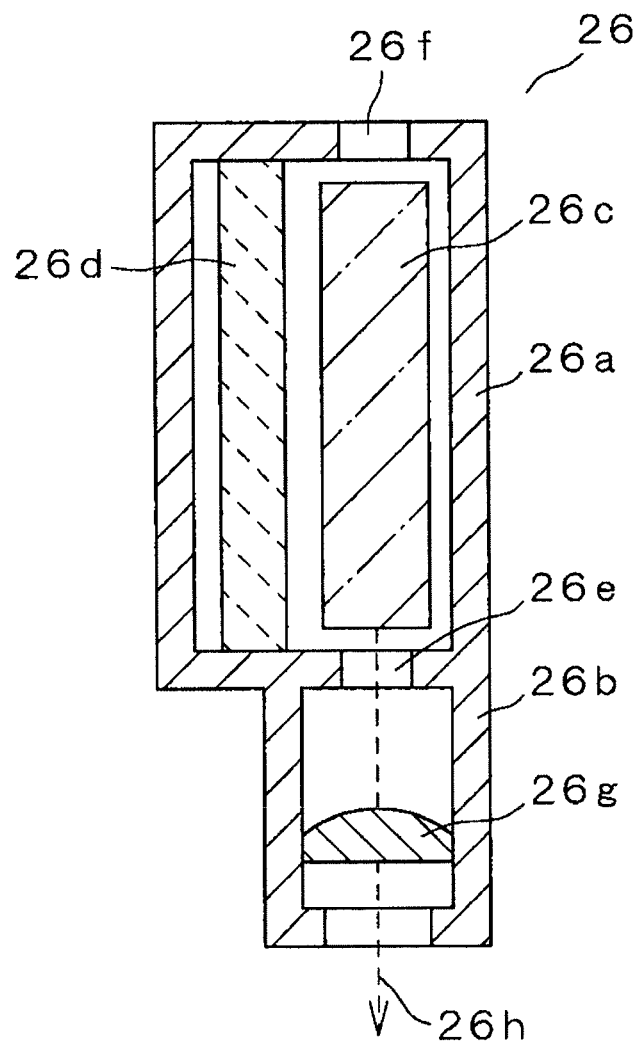
FIG. 21 is a cross sectional view of a laser emitting device of the blood test apparatus according to embodiment 1 of the present invention.

FIG. 21 is a cross sectional view of laser emitting device 26. Laser emitting device 26 includes an oscillating tube 26a and tubular body 26b coupled to oscillating tube 26a. An Er:YAG (yttrium, aluminium, garnet) laser crystal 26c and light source 26d are housed in oscillating tube 26a. Partially transmitting mirror 26e having a transmissivity of 3% to 15% is mounted on one end of oscillating tube 26a, and total reflecting mirror 26f having a transmissivity equal to or more than 0.5% is mounted on the other end of oscillating tube 26a. Convex lens 26g is mounted in tubular body 26b ahead of partially transmitting mirror 26e and arranged such that laser light 26h can focus on a position below skin 10 and close to the surface of skin 10 of the patient.

Next, the operation of laser emitting device 26 will be described. When the patient depresses puncturing button 26j (see FIG. 2 to FIG. 4 and FIG. 22), high voltage generating circuit 27h (see FIG. 22) is activated to excite excitation light source 26d. Light emitted from this light source 26d enters Er:YAG laser crystal 26c. Here, the light is continuously reflected by total reflecting mirror 26f, partially transmitting mirror 26e and Er:YAG laser crystal 26c, passing through them, and is amplified. A part of this amplified laser light passes through partially transmitting mirror 26e by induced emission. Laser light 26h passing through partially transmitting mirror 26e is emitted through lens 26g, and focuses on a position near the surface of skin 10. The depth of puncturing is preferably 0.6 mm to 1.5 mm from the surface of skin 10. Here, the depth is 0.8 mm in the present embodiment. In addition, the diameter of laser light is preferably 0.1 mm to 1.0 mm on the focal position. Here, the diameter is 0.2 mm to 0.3 mm in the present embodiment.

Since the present embodiment employs laser puncturing device 26 being capable of puncturing skin 10 of the patient out of touch, it has a lower risk than a needle puncture means which requires discarding and replacing used needles, and is very sanitary. Further, laser emitting device 26 has no moving components, so that there is little failure. Here, when the voltage for puncturing with laser light 26h is about 350 V, the patient feels less painful.

Figure 22:
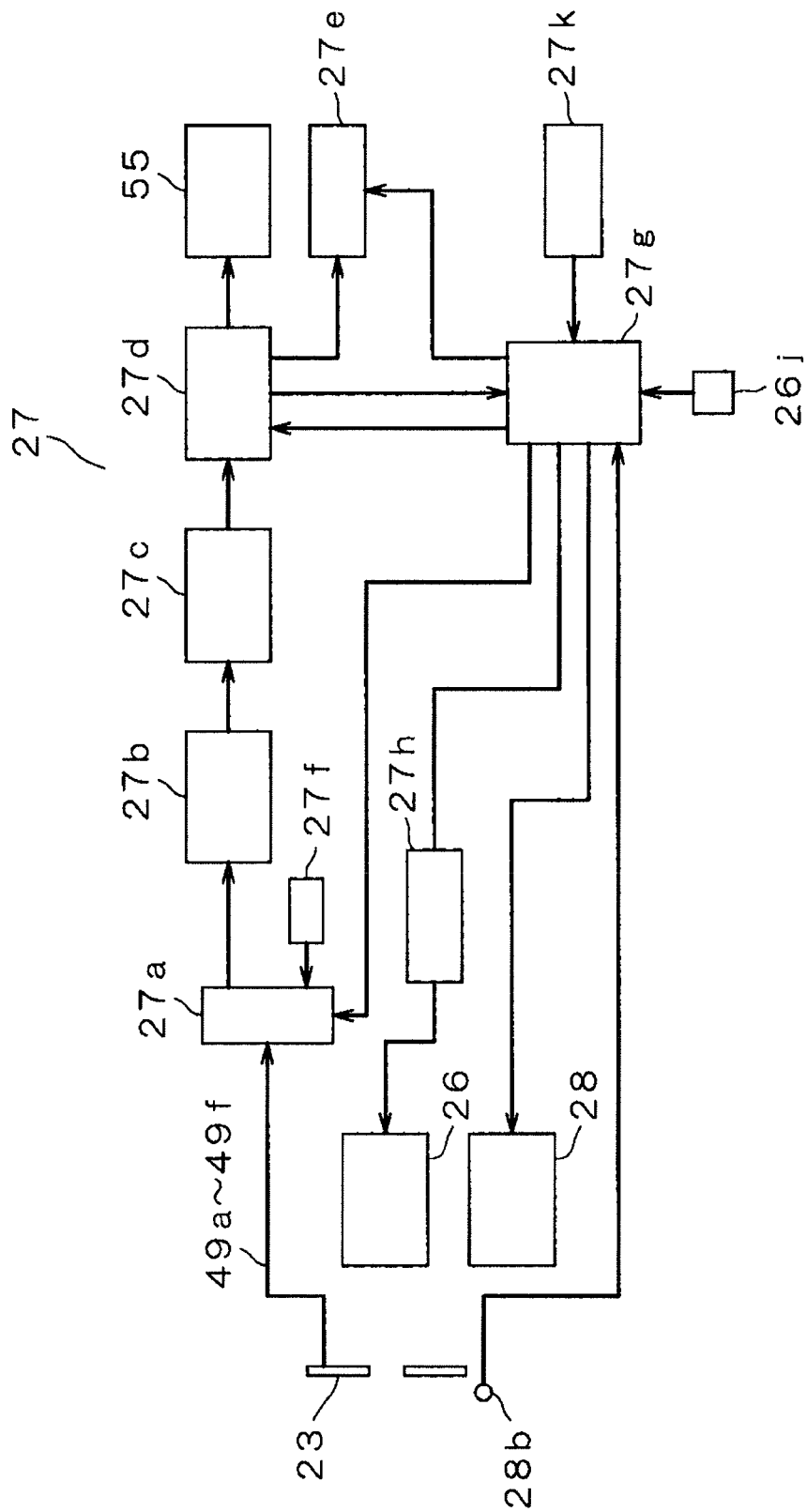
FIG. 22 is a block diagram showing an electrical circuit section and its peripheral parts according to embodiment 1 of the present invention.

FIG. 22 is a block diagram showing electrical circuit section 27 and its peripheral parts In FIG. 22, connection electrodes 41a to 45a and identification electrode 47a (see FIG. 14) are connected to switching circuit 27a through connectors 49a to 49f. The output of switching circuit 27a is input to current/voltage convertor 27b. Then, the output of current/voltage convertor 27b is input to computing section 27d through an analog/digital convertor (hereinafter referred to as A/D convertor). The output of computing section 27d is input to display section 55 made of liquid crystal and to communication section 27e. Reference voltage source 27f is connected to switching circuit 27a. Here, reference voltage source 27f may be a ground potential.

Control section 27g controls operation of the entire test apparatus according to the present invention. The output of control section 27g is input to high voltage generating circuit 27h connected to laser emitting device 26, a control terminal of switching circuit 27a, computing section 27d, communicating section 27e and pump 28. The outputs of puncturing button 26j, skin detecting sensor 28b, timer 27k and computing section 27d are input to control section 27g.

Next, the operation of electrical circuit section 27 will be described schematically. First, when skin 10 touches the under surface of second holder 25b, skin detecting sensor 28b detects that the skin is touching, and the operation of pump 28 that is a negative pressure unit is activated to suck in the skin.

Then, puncturing button 26j is depressed to puncture skin 10 by laser emitting device 26. Then, blood 11 exuded by the puncture is taken into sensor 23. Here, oxidation-reduction reaction with the reagent inside the sensor is electrochemically detected, and then the detected signal is electrically measured to measure the property of blood and so forth. In the measuring operation, detection electrode 41 (see FIG. 14) and current/voltage convertor 27b are electrically connected through connector 49 by switching circuit 27a.

Detection electrode 42 (see FIG. 14) for detecting an inflow of blood 11 is electrically connected to reference voltage source 27f. Then, a constant current is applied between the detection electrode 41 and the detection electrode 42. In this state, a current flows between detection electrodes 41 and 42 when blood 11 flows in. This current is converted into a voltage by current/voltage convertor 27b, and the voltage value is converted into a digital value by A/D convertor 27c. Computing section 27d detects whether blood 11 has sufficiently flown in, based on that digital value. When detecting that blood 11 sufficiently flows in, computing section 27d outputs information indicating this fact to control section 27g.

Here, at this time, the operation of pump 28 is turned off by a command from control section 27g. Next, glucose that is a component of blood will be measured. For measuring the glucose level, first, switching circuit 27a is switched by a command from control section 27g, and detection electrode 41 to be a working electrode for measuring glucose level is connected to current/voltage convertor 27b. In addition, detection electrode 43 to be a counter electrode for measuring the glucose level, is connected to reference voltage source 27f.

Here, for example, while the glucose in blood and its oxidation-reduction enzyme react for a given length of time, current/voltage convertor 27b and reference voltage source 27f are turned off. Then, after the certain period of time (1 to 10 seconds), a certain current (0.2 to 0.5 V) is applied between detection electrodes 41 and 43 by a command from control section 27g. By this means, a current flows between detection electrodes and 43. This current is converted into a voltage by current/voltage convertor 27b, and the voltage value is converted into a digital value by A/D convertor 27c and output to computing section 27d. Computing section 27d converts this digital value to glucose level.

Next, after the glucose level is measured, Hct value will be measured. In order to measure the Hct value, firstly, switching circuit 27a is switched by a command from control section 27g. Then, detection electrode 45 to be a working electrode for measuring the Hct value is connected to current/voltage convertor 27b. In addition, detection electrode 41 to be a counter electrode for measuring the Hct value is connected to reference voltage source 27f.

Next, a certain voltage (2V to 3V) is applied between detection electrodes 45 and 41 from current/voltage converter 27b and reference voltage source 27f, by a command from control section 27g. The current flowing between detection electrodes 45 and 41 is converted into a voltage by current/voltage convertor 27b, and the voltage value is converted into a digital value by A/D converter 27c and output to computing section 27d. Computing section 27d converts this digital value to Hct value.

By using the Hct value and glucose content resulting from measurement and referring to a calibration curve or calibration curve table determined in advance, glucose content is corrected by the Hct value and the correction result is displayed on display section 55. The calibration curve or calibration curve table is determined, based on identifying section 47 in sensor 23. In addition, the result corrected using the calibration curve or calibration curve table is transmitted from communicating section 27e to an injection device for injecting insulin. Although a radio wave may be used for this transmission, transmission is preferably performed by optical communication that does not interfere with medical equipment.

If the dose of insulin to administer is automatically set in an injection device by transmitting corrected measurement data from transmitting section 27e in this way, it is not necessary to set in the injection device the dose of insulin to be administered by the patient, which eliminates the burden with setting and human failures, such as setting error. Moreover, by way of communicating section 27e, it is possible to receive for version up of software and for update of setting data and to transmit measurement data to external equipment through the interface of an external PC and a communication device.

Although an example of glucose measurement has been described, the blood test apparatus is applicable to measure blood components other than glucose such as lactate acid or cholesterol levels by changing reagent 40 of sensor 23.

Figure 23:
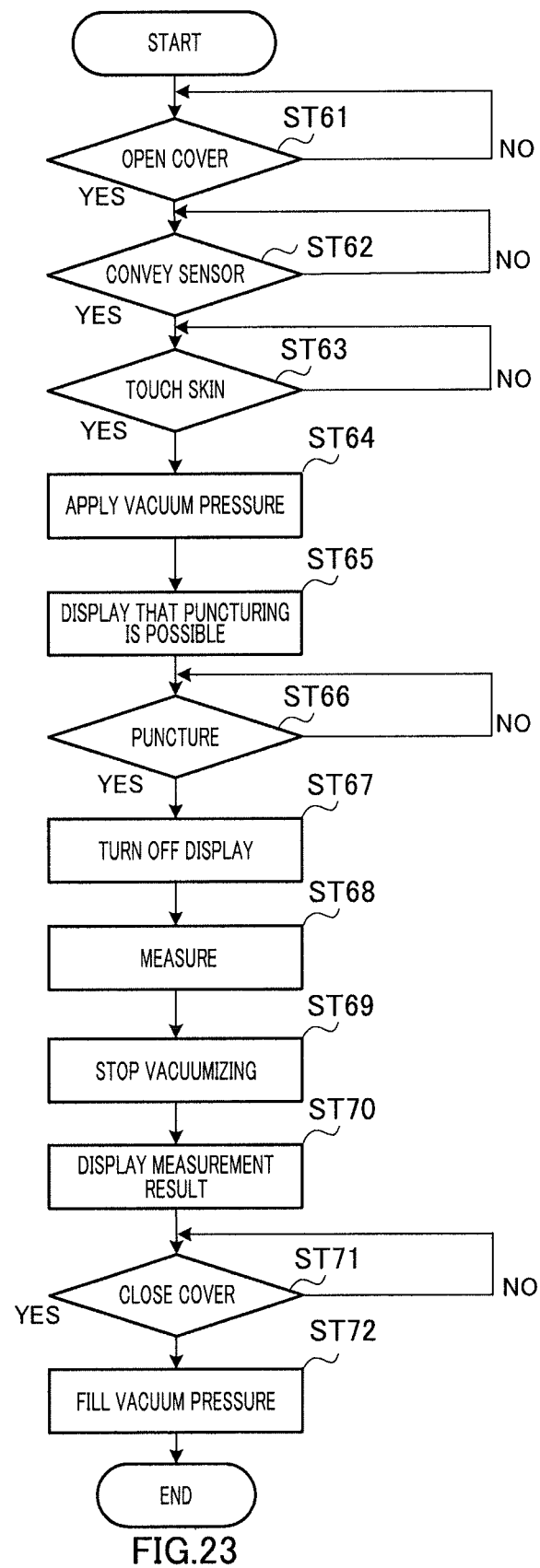
FIG. 23 is an operational flow chart of a test method of the blood test apparatus according to embodiment 1 of the present invention.

Next, a test method for blood test apparatus (see FIG. 1, for example) 21 will be described with reference to the operation flow chart of FIG. 23.

First, the patient opens cover 22b of the blood test apparatus 21 in step 61. When cover 22b is opened, shutter 24n of sensor outlet 24a provided in cartridge 24 opens in conjunction with the opening of cover 22b (see FIG. 8 to FIG. 11).

When cover 22b is opened (step 61: YES), the patient moves slider plate 24k toward sensor outlet 24a in step 62. By this means, only one sensor, which is bottommost sensor 23 among stacked and stored sensors 23 is separated and conveyed from sensor outlet 24a to holding section 25. It is possible to check that sensor 23 has been conveyed by detecting electric conduction between connection electrode 43a and identification electrode 47a of sensor 23. Then, slider plate 24k returns to a standby state by a repulsive force of spring 24p, and thereby a preparation for conveying next sensor 23 is ready (see FIG. 8 to FIG. 11).

When sensor 23 has been conveyed (step 62: YES), in step 63, the patient touches blood test apparatus 21 with skin 10. Whether skin 10 touches blood test apparatus 21 can be checked based on the output of skin detecting sensor 28b (see FIG. 20).

When skin 10 touches blood test apparatus 21 (step 63: Yes), pump 28 is activated to apply a negative pressure to the inside of negative pressure chamber 28a formed by holding section 25 and skin 10 in step 64. The surface of skin 10 swells by the negative pressure. Here, 4 to 5 seconds is enough time to apply a negative pressure (See FIG. 20).

When a change in the current along with the operation of pump 28 is detected, or when a period of time determined in advance by timer 27k passes, blood test apparatus 21 determines that the surface of skin 10 in storing section 34 has swelled sufficiently, and the step moves to step 65.

In step 65, blood test apparatus 21 displays "puncturing is possible" on display 55 and waits until puncturing button 26j is depressed.

Then, when the patient depresses puncturing button 26j, blood test apparatus 21 punctures skin 10 by a built-in puncturing means in step 66. Here, regardless of depressing puncturing button 26j, blood test apparatus 21 may automatically puncture when the following conditions are satisfied: after a predetermined time period, a change in the current involved in operating the pump is detected; and the skin detecting sensor checks that the skin is not detached and so forth.

When the puncturing is completed (step 66: YES), in step 67, blood test apparatus 21 turns off once the display of step 65. Next, detecting section 37 of blood test apparatus 21 measures the blood sugar level of blood 11 and so forth exuding by puncturing skin 10 in step 68. Here, the time required for the measurement is about 3 to 5 seconds.

Next, blood test apparatus 21 turns off pump 28 in step 69, and displays the blood sugar level and so forth on display 55 in step 70. This is the end of measurement of blood 11. Here, the negative pressure operation is completed by the time when a measurement result is displayed, and then pump 28 is turned off. Alternatively, blood test apparatus 21 may turn off pump 28 at a time when blood 11 reaches detection electrode 42.

Next the patient closes cover 22b of blood test apparatus 21 in step 71. Shutter 24n of cartridge 24 is closed in conjunction with closing cover 22b, so that the sensor outlet 24a is closed.

When cover 22b is closed (step 71: YES), pump 28 is operated for a predetermined time period, so that the negative pressure in cartridge 24 becomes a predetermined atmospheric pressure in step 72.

As described above, according to the present embodiment, puncturing is performed after the sensor is conveyed, so that the efficiency of a series of blood test operations, including puncturing, sampling blood and measurement can be significantly improved, and also the reliability can be significantly improved.

Moreover, the finger is not likely to come off the blood test apparatus from when the patient punctures his/her skin to when the blood test is completed, so that the measurement can be reliably conducted, without danger such that other places are stained with blood.

In addition, since blood 11 exuding by puncturing is stored in storing section 34, the blood sugar level is reliably measured using blood 11, so that the burden on the patient can be minimized.

Here, a sensor for detecting whether cover 22b is open or closed may be provided in blood test apparatus 21, and a warning may be issued to the patient with a buzzer and a flashing LED after a certain period of time passes since the sensor detects that cover 22b is open.

Moreover, another sensor for detecting the opening and closing angle of cover 22b may be separately provided, and puncturing may be prohibited when cover 22b is opened beyond the first resting position. By this means, even if the patient and so forth could depress puncturing button 26j by mistake, laser light 26h is not emitted outside, so that the safety can be assured.

Furthermore, cover 22b may be provided with a cushioning material on the side facing a table when the apparatus is put on the table, thereby a shock may be cushioned and the apparatus is protected. In addition, the cover itself may be formed of a cushioning material.

Figure 24:
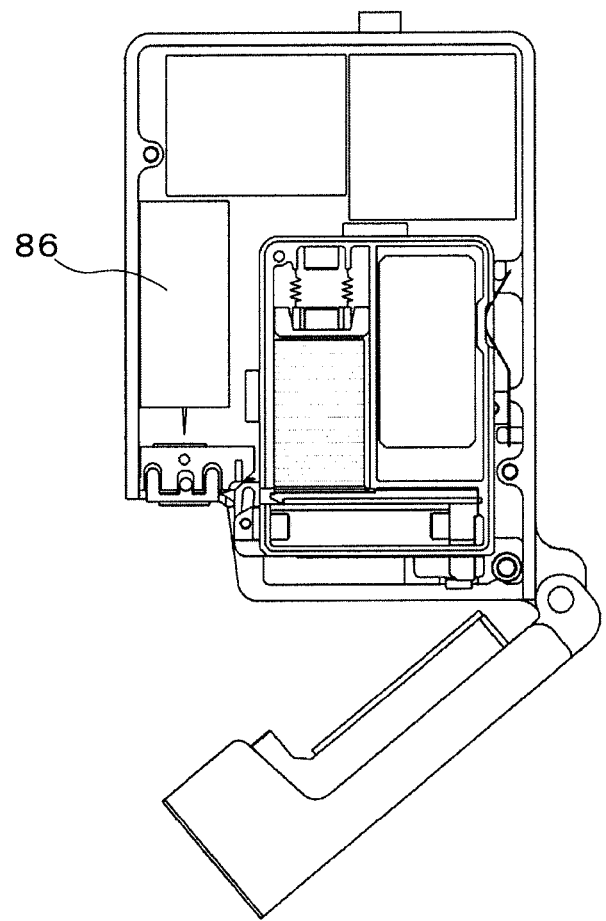
FIG. 24 is a cross sectional view of the blood test apparatus according to embodiment 1 of the present invention.

Here, although an instance has been described above with the present embodiment where laser emitting device 26 is used as a puncturing means, the present invention is not limited to this regard and it is equally possible to use a needle puncturing device 86 for puncturing with a puncture needle as the puncturing means as shown in FIG. 24. By using needle puncturing device 86, the consumption of battery 29 can be reduced.

Embodiment 2

Although a type of blood test apparatus having a holding section fixed to the housing has been described with embodiment 1, another type of blood test apparatus having a holding section integrated with the cartridge will be described with the present embodiment. Here, the same components as in embodiment 1 will be assigned the same reference numerals and explanation thereof will be omitted.

Figure 25:
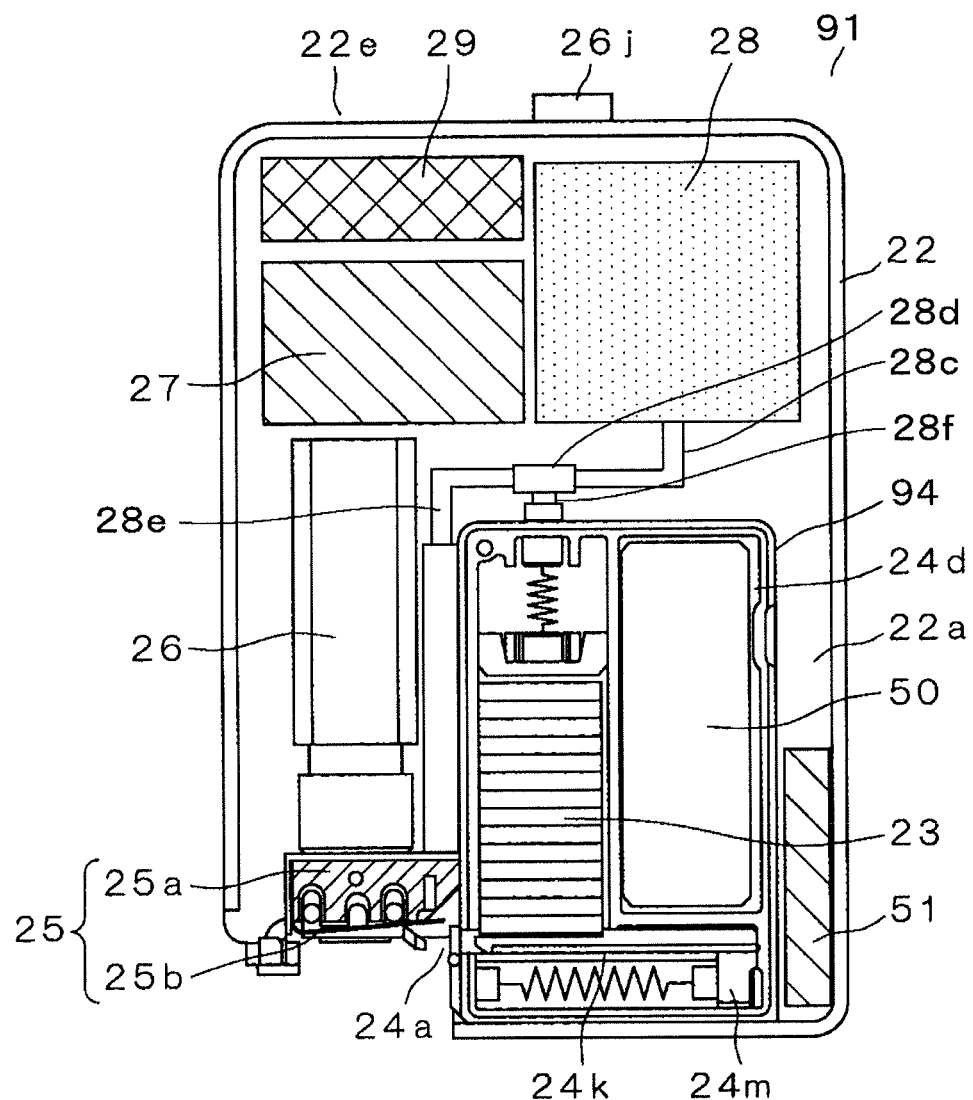
FIG. 25 is a cross sectional view of a blood test apparatus according to embodiment 2 of the present invention.
Figure 26:
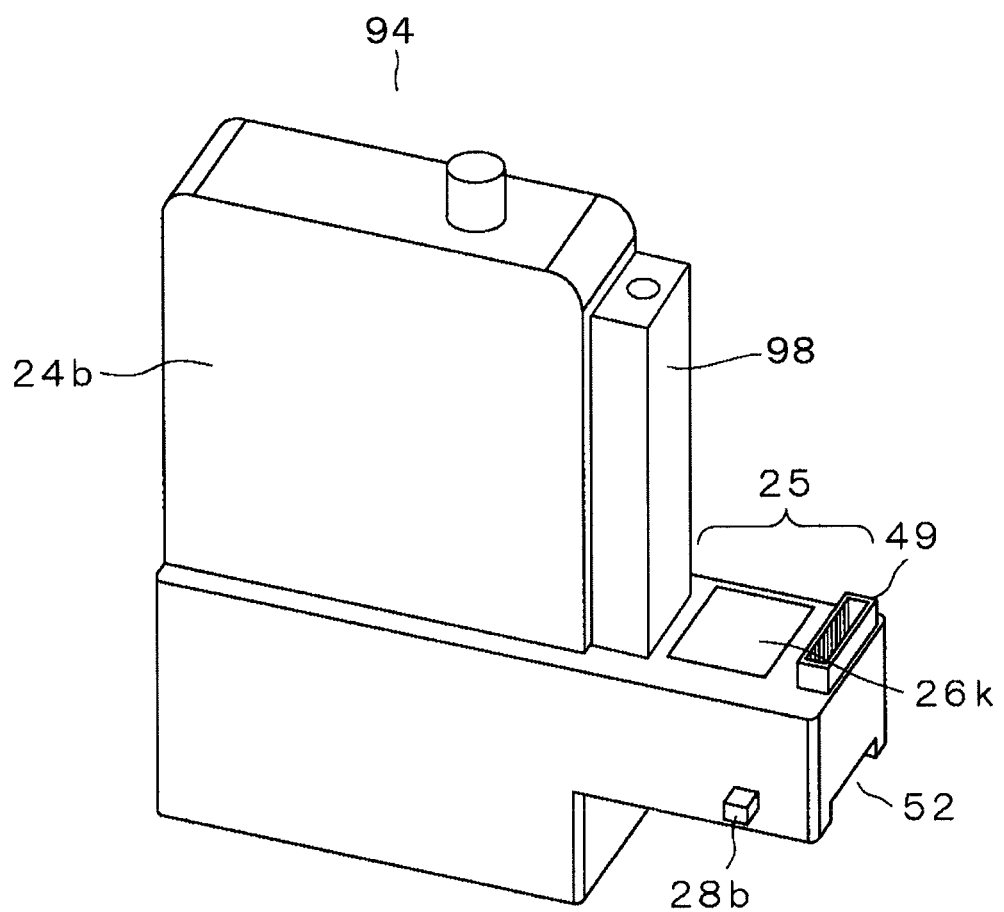
FIG. 26 is an external perspective view of a holding section-integrated cartridge according to embodiment 2 of the present invention.
Figure 27:
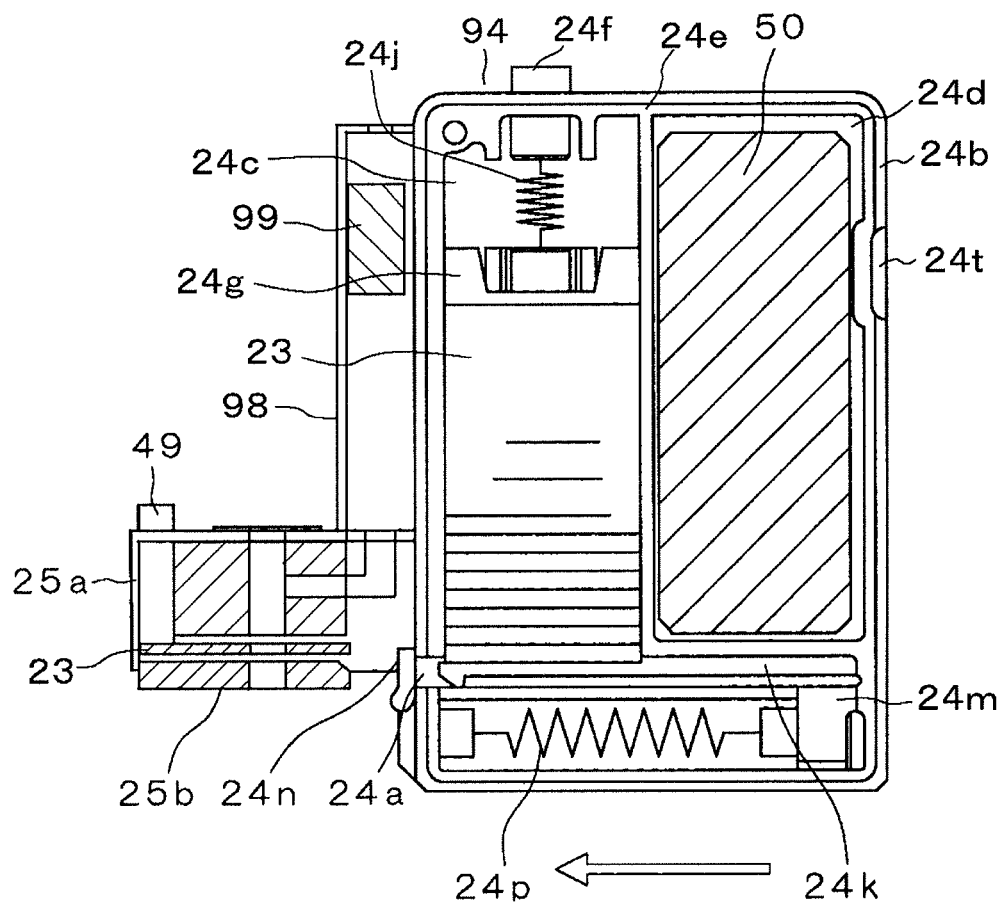
FIG. 27 is a cross sectional view of the holding section-integrated cartridge according to embodiment 2 of the present invention.

FIG. 25 is a cross sectional view of blood test apparatus 91 according to the present embodiment. FIG. 26 is an external perspective view of cartridge 94 integrated with the holding section. FIG. 27 is a cross sectional view of cartridge 94 integrated with the holding section. FIG. 27 shows the rear face of FIG. 26.

Here, FIG. 25 shows an instance where cover 22b does not move with slider plate 24k for conveying sensor 23 unlike FIG. 1. In addition, cover 22b is not shown for ease of understanding of the drawing.

As shown in FIG. 26, cartridge 94 includes case 24b, holding section 25, connector 49, sensor ejecting port 52, skin detecting sensor 28b, lens protecting member 26k and passage 98.

By subjecting the wall surface of passage 98 to antibacterial treatment, carbonization odor of evaporated materials can be alleviated. Here, a photocatalyst may be attached instead of the antibacterial treatment in order to remove odor. In this case, by providing a lighting window on case 24b, external light (ultraviolet light) will be emitted to the photocatalyst.

Now, the principle of deodorization with the photocatalyst will be described. When the light is emitted to the photocatalyst, electrons get out from the surface of the photocatalyst. Holes are generated in the positions from which the electrons get out. These holes have strong oxidizability and take electrons away from hydroxide ions in the moisture of the air. The hydroxide ions from which electrons are taken away become very unstable OH radical. The OH radical takes the electrons from adjacent organic matter, and tries to achieve its stability because of its very strong oxidizability. Thus the organic matter from which electrons are taken away is decoupled, and then finally becomes odorless carbon dioxide, water and so forth, and diffuses in the air. In addition, a deodorization member such as activated carbon for sucking in the evaporated material may be attached to passage 98 to remove the evaporated material.

In addition, dust may be collected by disposing a plurality of electrodes in passage 98 and applying a voltage (i.e. applying a potential difference) to the plurality of electrodes. Since the evaporated material containing fine particles is captured by the plurality of charged electrodes by applying the voltage, clean air without any odor can be obtained.

Moreover, filter 99 (see FIG. 27) may be attached to the inside of passage 98. By attaching filter 99, the evaporated material produced by puncturing may be prevented from entering case 24b of cartridge 24b. Here, it is preferable to provide filter 99 in a position near housing section 25, not in a position near valve 28d.

When cartridge 94 is mounted in blood test apparatus 91, connector 49 provided in first holder 25a constituting holding section 25 and a contacting section (not shown in the drawing) provided in housing 22 contact and electrically connect. By this means, a signal of sensor 23 can be transmitted to electrical circuit section 27.

Lens protecting member 26k (see FIG. 26) is mounted on the upper surface of holding section 25. As described in embodiment 1, the evaporated material produced by puncturing with laser light 26h is ejected through side hole 25n of first holder 25a and passage 98 for a negative pressure by the operation of pump 28. Therefore, little stain and dust adhere to lens protecting member 26k provided on upper surface of holding section 25, and the evaporated material hardly reaches lens protecting member 26k. Consequently, the stain on lens protecting member 26k can be reduced, so that the optical transparency of lens protecting member 26k does not deteriorate.

As described above, by integrating holding section 25 sandwiching sensor 23 with cartridge 94, the positional relationship between sensor 23 and holding section 25 does not change, so that the accuracy of positioning is stabilized and the reliability of mounting sensor 23 is significantly improved.

In addition, since cartridge 94 is replaced when the stacked and stored sensors 23 are run out, lens protecting member 26k is replaced at the same time. Therefore, it is not necessary to independently replace only lens protecting member 26k.

Here, although an instance with one passage 98 has been described, the present invention is not limited to this regard and a plurality of passages may be provided. In addition, a plurality of side holes 25 are provided on first holder 25a, and the other passage than passage 98, which connects pump 28 and first holder 25a is provided, therefore a negative pressure may be applied to first holder 25a through the plurality of passages.

Embodiment 3

Although a type of blood test apparatus having a holding section fixed to the housing has been described with embodiment 1, another type of blood test apparatus having a second holder integrated with the cartridge will be described. Here, the same components as in embodiment 1 and 2 will be assigned the same reference numerals and explanation thereof will be omitted.

Embodiment 3-1

Figure 28:
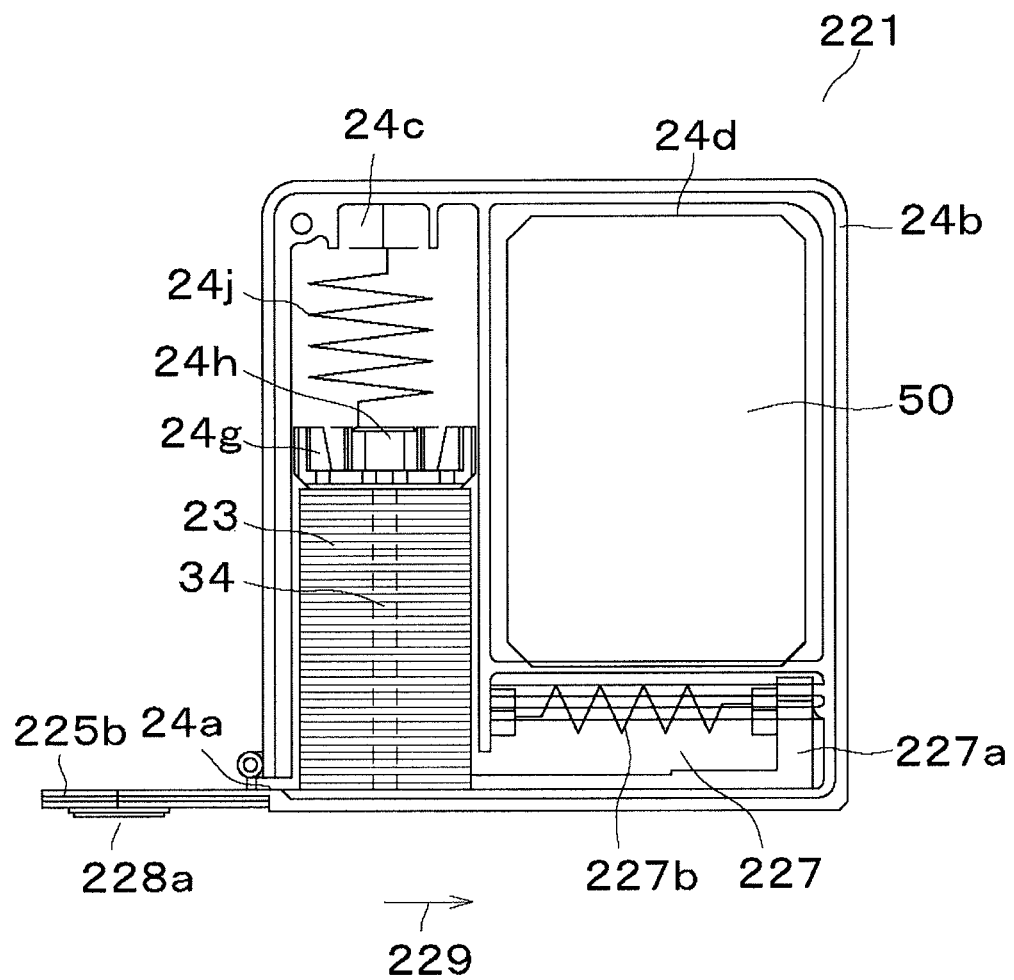
FIG. 28 is a cross sectional view of a cartridge according to embodiment 3 of the present invention.

FIG. 28 is a cross sectional view of a cartridge 221 according to the present embodiment. As shown in FIG. 28, second holder 225b is mounted on cartridge 221. Hole 228a is provided on second holder 225b, which communicates with a position facing storing section 34 of sensor 23 when sensor 23 is set.

Figure 29A:
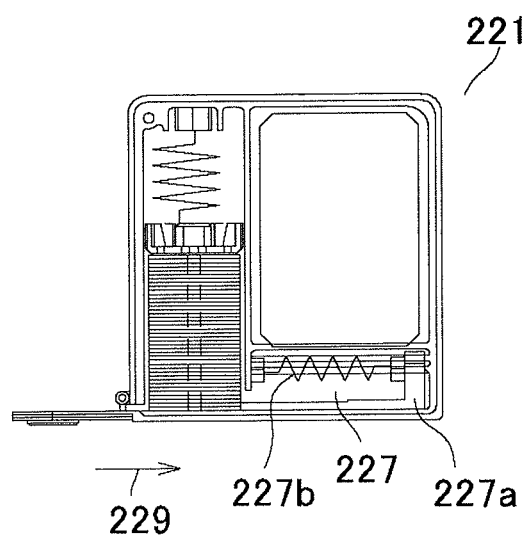
FIG. 29A is an explanatory drawing of a sensor moving operation according to embodiment 3 of the present invention.

Next, the conveying operation of sensor 23 according to the present embodiment will be described with reference to FIG. 29. FIG. 29A shows a state before sensor 23 is conveyed (initial state). At this time, slide plate 227a is biased toward arrow 229 by the force of spring 227b.

Figure 29B:
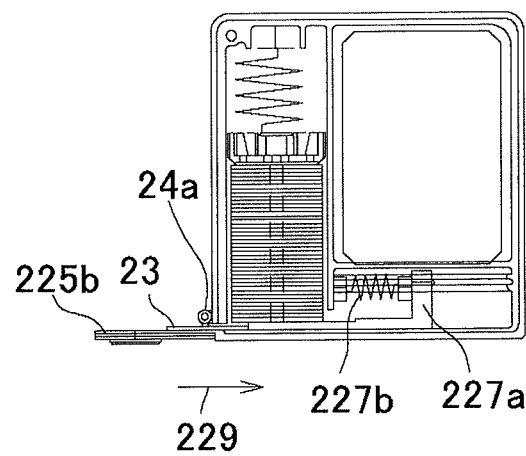
FIG. 29B is an explanatory drawing of a sensor moving operation according to embodiment 3 of the present invention.
Figure 29C:
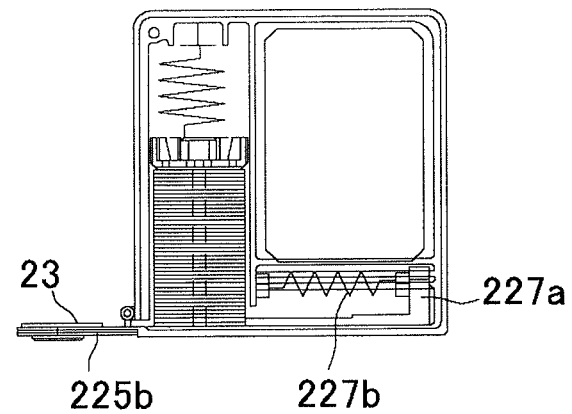
FIG. 29C is an explanatory drawing of a sensor moving operation according to embodiment 3 of the present invention.

Next, in order to convey sensor 23 onto second holder 225b, slide plate 227a is moved toward outlet 24a (opposite arrow 229) against the force of spring 227b as shown in FIG. 29B. At this time, the bottommost sensor 23 among stacked and stored sensors 23 placed on slider plate 227a is conveyed from sensor outlet 24a to holding section 225. After sensor 23 has been moved and sensor 23 is set onto second holder 225, slide plate 227a returns to the original position (initial state) by the force of spring 227b.

Thus, according to the present embodiment, since second holder 225b directly touching the skin is integrated with cartridge 221, consequently second holder 225b is replaced every time cartridge 221 is replaced. Therefore, it does not require maintenance, for example, periodic cleaning of second holder 225b, so that the burden of maintenance can be significantly alleviated.

Embodiment 3-2

In the present embodiment, second holder 235b of cartridge 231 may be pivotally mounted around supporting point 232c as shown in FIG. 30. Second holder 235b can be folded because of being pivotally mounted.

Figure 30A:
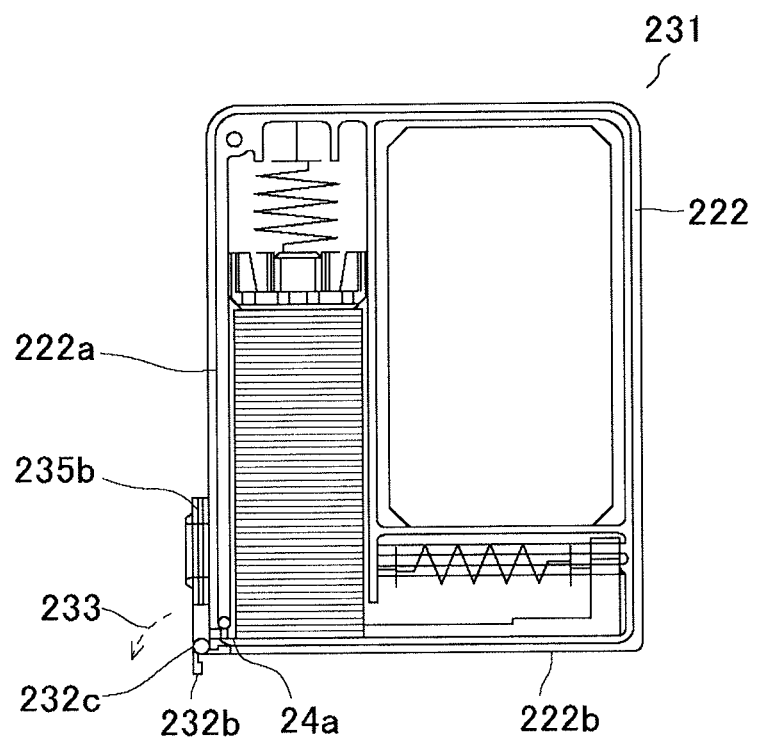
FIG. 30A is a cross sectional view of the cartridge according to embodiment 3 of the present invention.
Figure 30B:
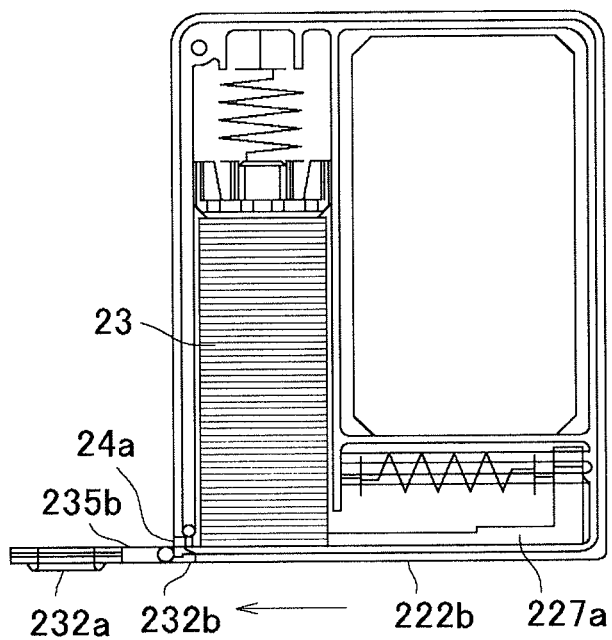
FIG. 30B is a cross sectional view of the cartridge according to embodiment 3 of the present invention.

FIG. 30A shows an instance where second holder 235b is folded toward lateral surface 222a of sensor chamber 224 (the left hand in FIG. 30A) of case 222. In this state, when pawl 232b is pressed down bottom surface 222b, second holder 235b turns counterclockwise 90 degrees in the direction of arrow 233 around spindle 232c. Then, as shown in FIG. 30B, second holder 235b is coupled to outlet 24a and disposed on the extension line of slide plate 227a, that is, second holder 235b is disposed in the horizontal direction as with slide plate 227a. At this time, pawl 232b of second holder 235b is locked and fixed to bottom surface 222b of case 222.

Here, when cartridge 231 is inserted in the blood test apparatus, second holder 235b may automatically rotate. Alternatively, pawl 232b is previously rotated 90 degrees by hand, and then cartridge 231 may be inserted in the blood test apparatus.

Thus, before being inserted into the blood test apparatus, second holder 235b of cartridge 231 is folded toward side surface 222a, so that the handling becomes easier because there is not any undesired convex part.

Embodiment 3-3

In the present embodiment, second holder 245b may be stored in case 222 of cartridge 241 as shown in FIG. 31.

Figure 31A:
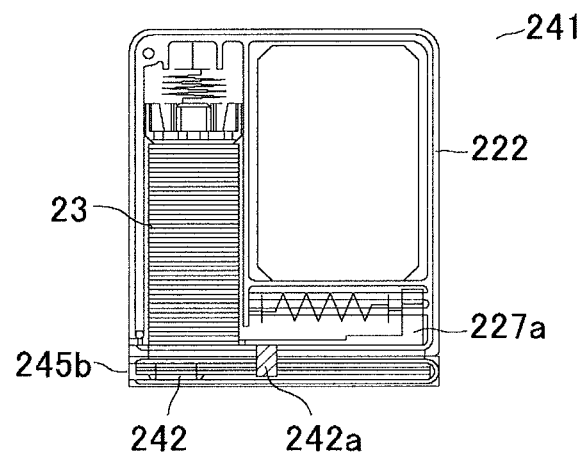
FIG. 31A is a cross sectional view of the cartridge according to embodiment 3 of the present invention.

FIG. 31A shows an instance where cartridge 241 is unused, and second holder 245b is stored in case 222. Therefore, cartridge 241 is compact in such unused state, so that the handling becomes easier. Pawl 242a for locking is mounted on the rear end of second holder 245b.

Figure 31B:
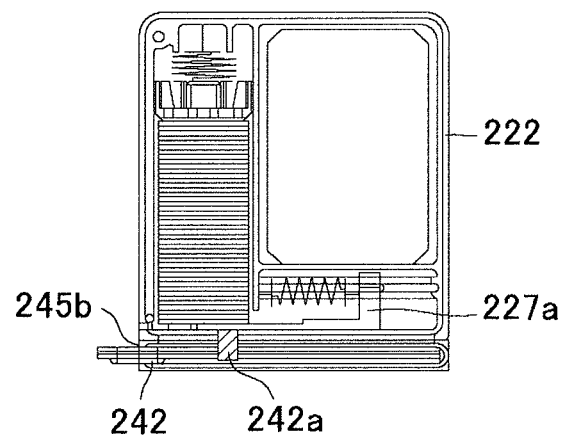
FIG. 31B is a cross sectional view of the cartridge according to embodiment 3 of the present invention.

FIG. 31B a cross sectional view showing a state where second holder 245b stored in case 222 is being pushed out toward outlet 242b of second holder 245b. Second holder 245b is pushed out from outlet 242b by pushing out pawl 242a with the tip of slide plate 227a.

Figure 31C:
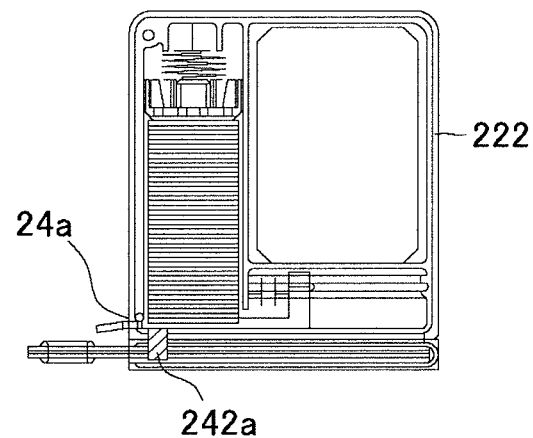
FIG. 31C is a cross sectional view of the cartridge according to embodiment 3 of the present invention.

FIG. 31C is a cross sectional view showing a state where second holder 245b has been pushed out. At this time, slide plate 227a returns to the original position once, and the second holder 245b is fixed in the position to which the second holder is pushed out. In addition, second holder 245b is inserted in cartridge 241. Here, second holder 245b may be inserted in cartridge 241, and later pushed out again.

Moreover, second holder 245b may be pushed out such that second holder 245b is automatically pushed outside the case using a pushing-out mechanism provided in the blood test apparatus at the same time when cartridge 241 is inserted in the blood test apparatus.

Embodiment 3-4

Figure 32:
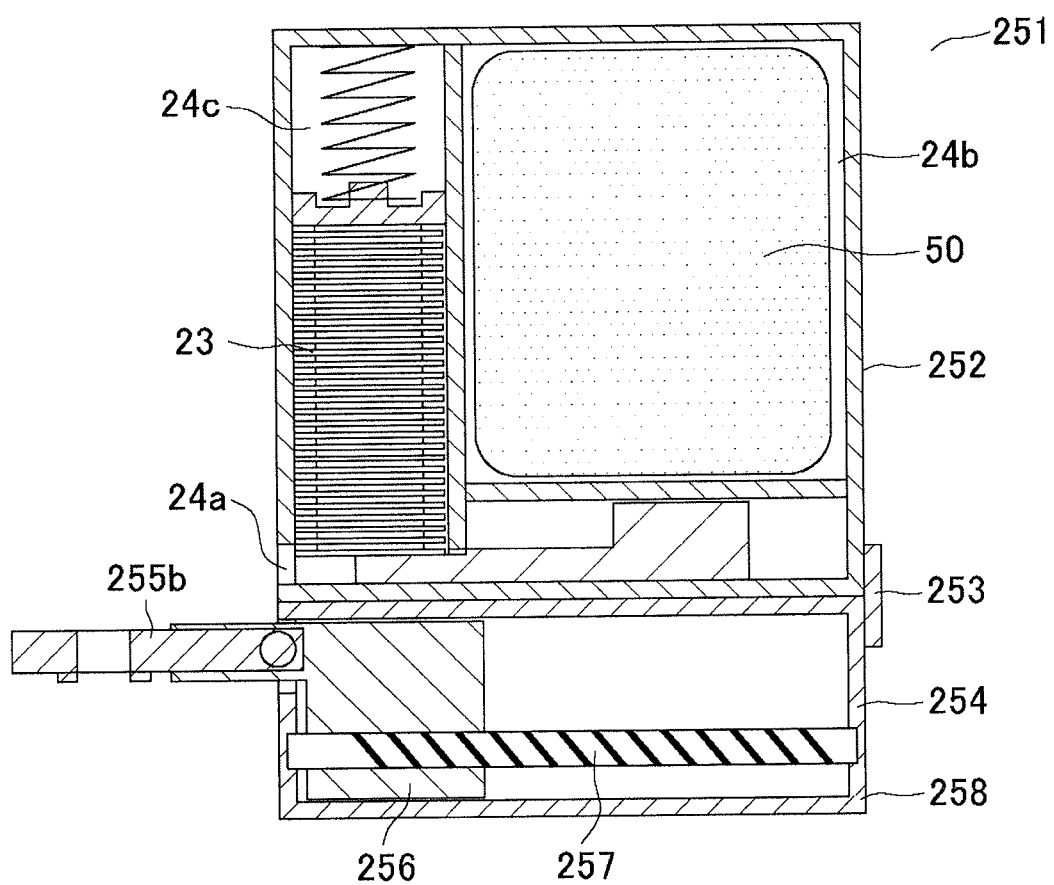
FIG. 32 is a cross sectional view of the cartridge according to embodiment 3 of the present invention.

In the present embodiment, as shown in FIG. 32, it is possible to have holder unit 254 removably mounted to main body 252 of cartridge 251 through coupling section 253. Since this holder unit 254 is removably mounted to main body 252 of cartridge 251, holder unit 254 can be independently used more than once.

Holder unit 254 is mainly composed of second holder 255b, holder supporting section 256 coupled to second holder 255b, slide guide 257 for sliding holder supporting section 256 and case 258.

Figure 33A:
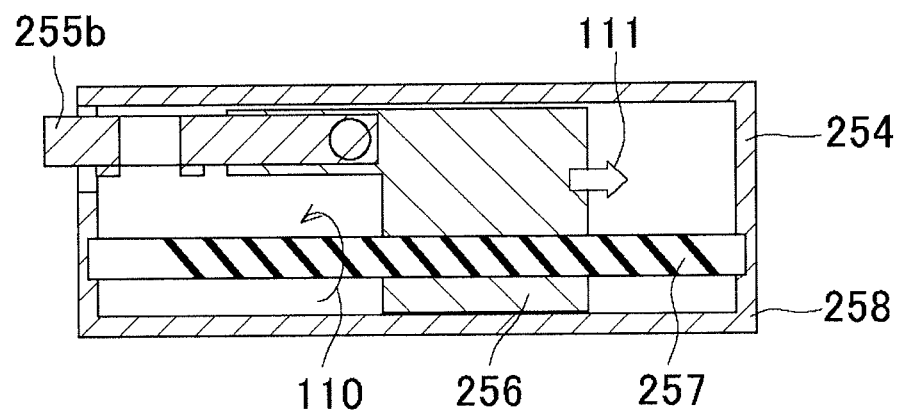
FIG. 33A is a cross sectional view of the cartridge according to embodiment 3 of the present invention.

FIG. 33A shows a state where second holder 255b is housed in case 258. Slide guide 257 is rotated in the direction of arrow 110, so that holder supporting section 256 moves in the direction of arrow 111. When holder supporting section 256 moves, second holder 255b coupled to holder supporting section 256 also moves in the same direction, so that second holder 255b is housed in case 258. Consequently, the apparatus becomes compact when holder unit 254 is unused, and the handling becomes easier.

Figure 33B:
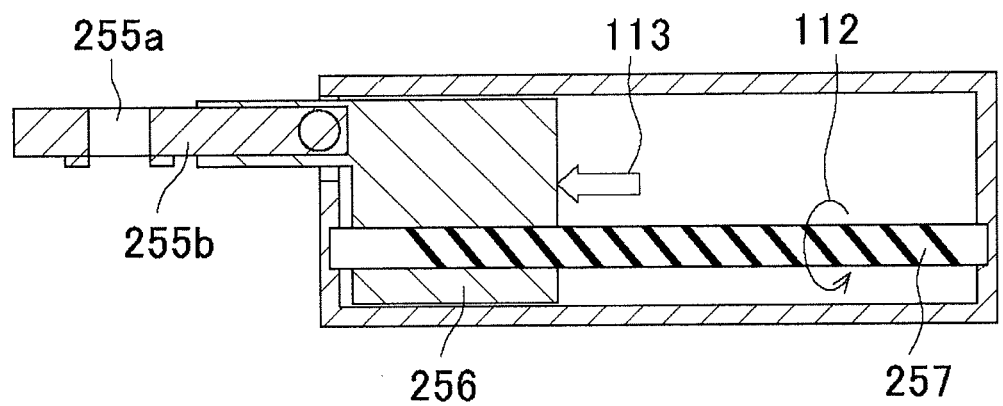
FIG. 33B is a cross sectional view of the cartridge according to embodiment 3 of the present invention.

FIG. 33B shows a state where second holder 255b is pushed out from case 258, and holder unit 254 is used in this state. Slide guide 257 is rotated in the direction of arrow 112, so that holder supporting section 256 moves in the direction of arrow 113. When holder supporting section 256 moves, second holder 255b coupled to holder supporting section 256 also moves to the same direction, so that second holder 255b is pushed out from case 258 and is available. Here, when being inserted in the blood test apparatus, second holder 255b can be projected by rotating slide guide 257 in the direction of arrow 112.

FIG. 34 is a cross sectional view explaining a process to project second holder 255b. In addition, FIG. 34 shows a state where holder unit 254 is coupled to main body 252 through coupling section 253.

Figure 34A:
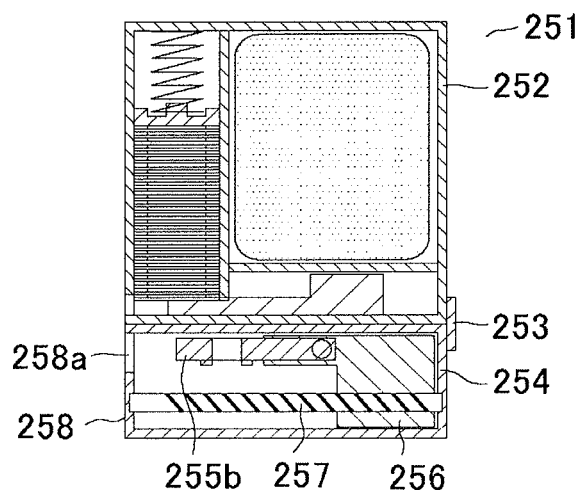
FIG. 34A is a cross sectional view of the cartridge according to embodiment 3 of the present invention.

FIG. 34A shows a state where second holder 255b is housed in case 258. Before being inserted in the blood test apparatus, cartridge 251 can house second holder 255b in case 258, so that there is any undesired convex part and the handling becomes easier.

Figure 34B:
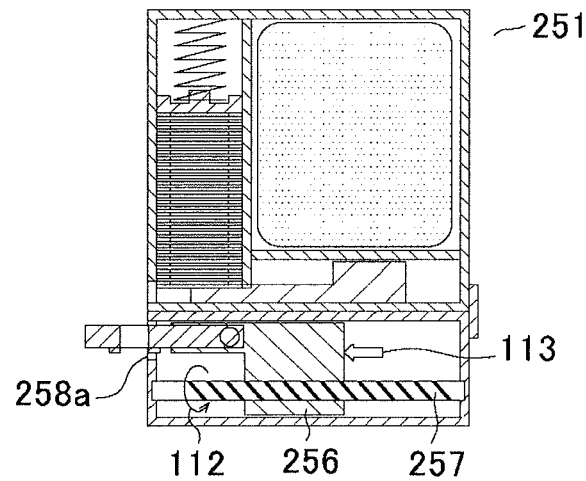
FIG. 34B is a cross sectional view of the cartridge according to embodiment 3 of the present invention.

FIG. 34B shows a state where second holder 255b is being brought out from case 258. Slide guide 257 is rotated in the direction of arrow 112 to move holder supporting section 256 in the direction of arrow 113, so that second holder 255b coupled to holder supporting section 256 projects from outlet 258a.

Figure 34C:
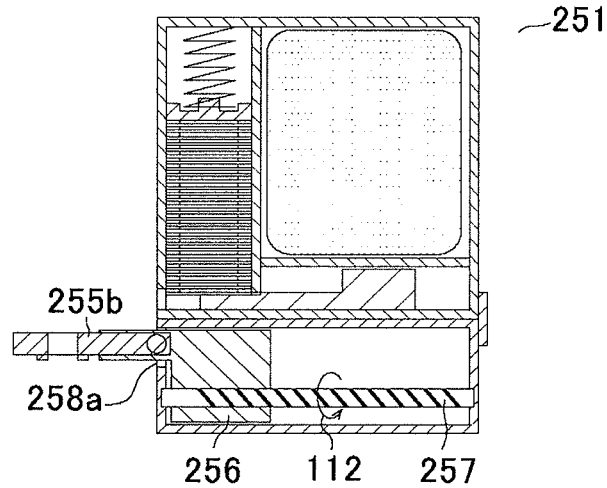
FIG. 34C is a cross sectional view of the cartridge according to embodiment 3 of the present invention.

FIG. 34C shows a state where second holder 255b is pushed out from case 258. Slide guide 257 is further rotated in the direction of arrow 112 to entirely project second holder 255b from outlet 258a, so that cartridge 251 becomes available.

FIG. 35 is a cross sectional view explaining a process to convey sensor 23 after cartridge 251 is inserted in the blood test apparatus.

Figure 35A:
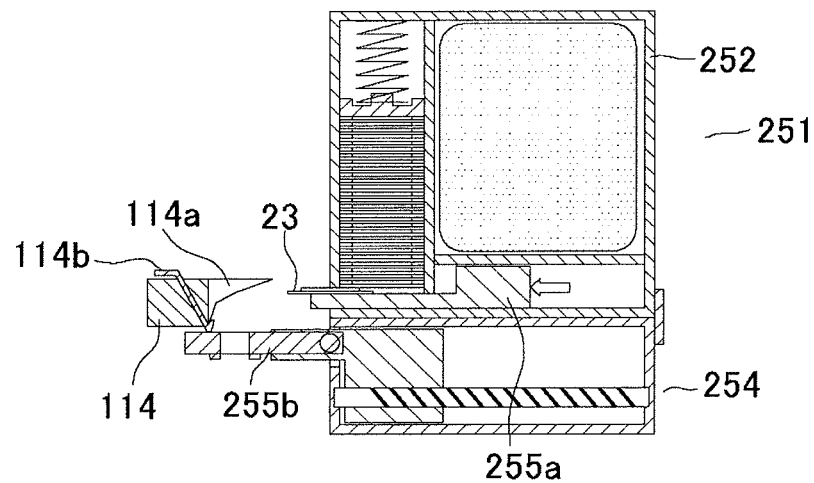
FIG. 35A is a cross sectional view of the cartridge according to embodiment 3 of the present invention.

FIG. 35A is a cross sectional view showing a state where slide plate 115a is conveying sensor 23 toward second holder 255b.

When cartridge 251 has holder unit 254, there is a thickness produced by the case of cartridge 251 and the case of holder unit between main body 252 and holder unit 254. Therefore, first holder 114 is provided with guide 114a that guides sensor 23 to the second holder 225b side. Connector 114b is abutted on a terminal formed by sensor 23.

Figure 35B:
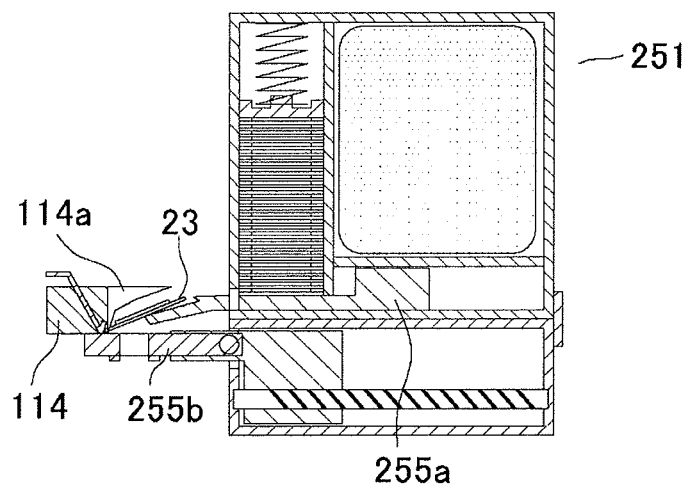
FIG. 35B is a cross sectional view of the cartridge according to embodiment 3 of the present invention.

FIG. 35B is a cross sectional view showing a state where sensor 23 is entirely pushed out using slide plate 115a. Sensor 23 is guided to second holder 255b along guide 114a.

Figure 35C:
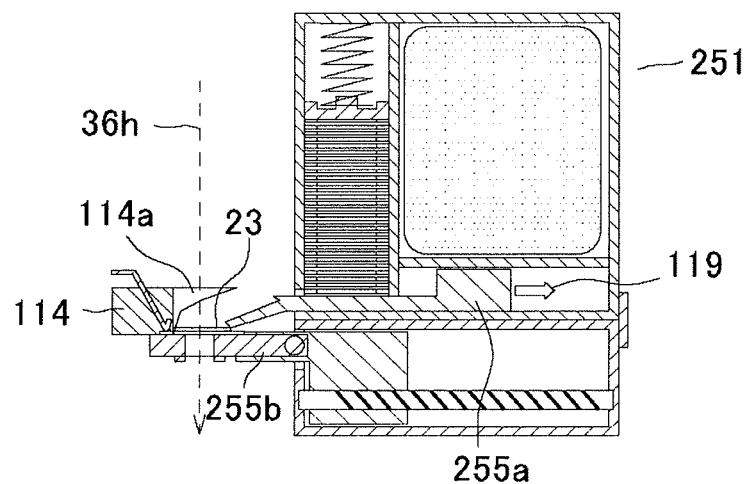
FIG. 35C is a cross sectional view of the cartridge according to embodiment 3 of the present invention.

Next, as shown in FIG. 35C, slide plate 115a is returned in the direction of arrow 119 to set sensor 23 onto second holder 255b.

FIG. 36 is a cross sectional view explaining a state where second holder 255b is removed from holder unit 254.

Figure 36A:
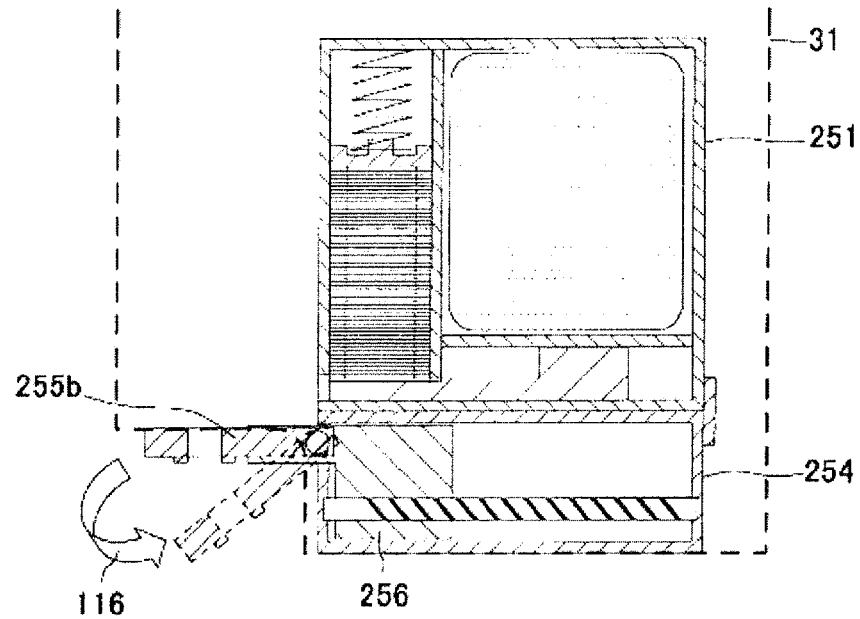
FIG. 36A is a cross sectional view of the cartridge according to embodiment 3 of the present invention.

In FIG. 36A, second holder 255b is bent toward arrow 116 to remove second holder 255b from holder supporting section 256. This removed second holder 255b can be discarded as is. Therefore, even if second holder 255b is stained with blood, holder unit 254 and the blood test apparatus are not stained. In addition, since second holder 255b is heavily soiled as the usage count is increased, it is possible to replace with a new one by removing second holder 255b in this way.

Figure 36B:
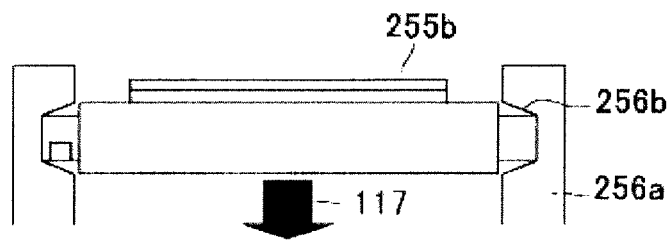
FIG. 36B is a cross sectional view of the cartridge according to embodiment 3 of the present invention.

Second holder 255b is fitted in concave part 256b of holding section 256a coupled to holder supporting section 256 and is supported by holder supporting section 256 as shown in FIG. 36B. In order to remove second holder 255b, a force is applied to second holder 255b in the direction of arrow 117 in this state. That is, second holder 255b is bent in the direction of arrow 116 in FIG. 36A.

Figure 36C:
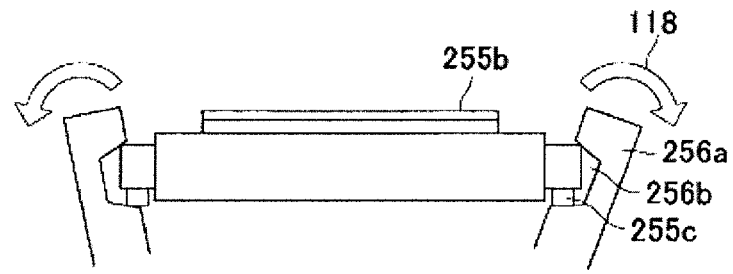
FIG. 36C is a cross sectional view of the cartridge according to embodiment 3 of the present invention.

Consequently, second holder 255b rotates as shown in FIG. 36C. This rotation causes convex parts 255c provided on both sides of second holder 255b to widen holding section 256a in the direction of arrow 118. When holding section 256a is widened in the direction of arrow 118, the engagement between convex parts 255c and concave parts 256b is released, so that second holder 255b can be removed from holder supporting section 256 and discarded as it is. Alternatively, by reversely performing the operation, new second holder 255b may be mounted on holding section 256a. As described above, according to the present embodiment, the resource can be efficiently utilized.

Embodiment 4

Although a type of blood test apparatus having a cartridge housed in the housing has been described in embodiment 1 to embodiment 3, another type of blood test apparatus having a cartridge externally attached to the housing will be described in the present embodiment. Here, the same components as in embodiment 1 to embodiment 3 will be assigned the same reference numerals and explanation thereof will be omitted.

Figure 37:
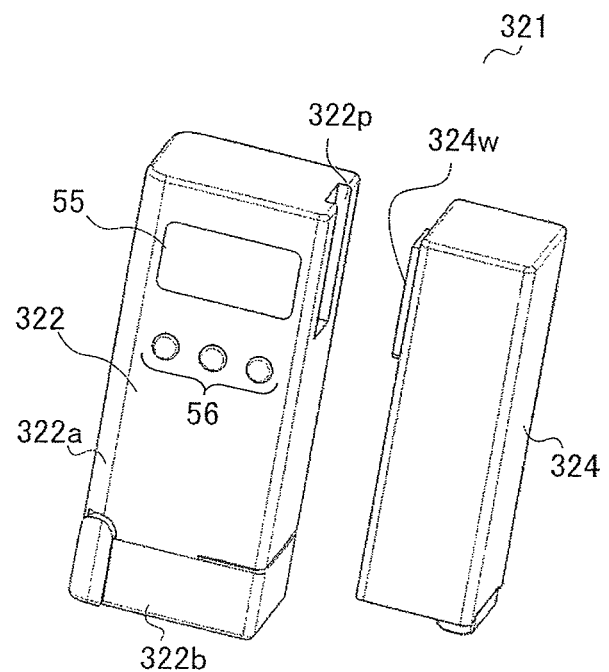
FIG. 37 is a perspective view of a blood test apparatus according to embodiment 4 of the present invention.
Figure 38:
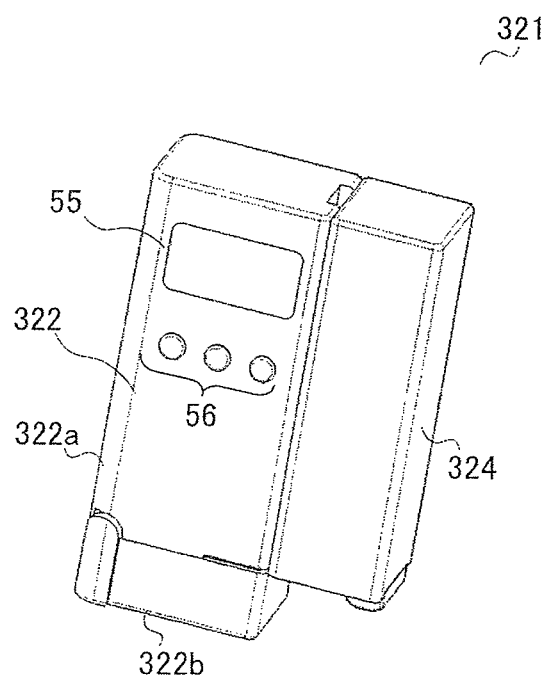
FIG. 38 is a perspective view of the blood test apparatus according to embodiment 4 of the present invention.
Figure 39:
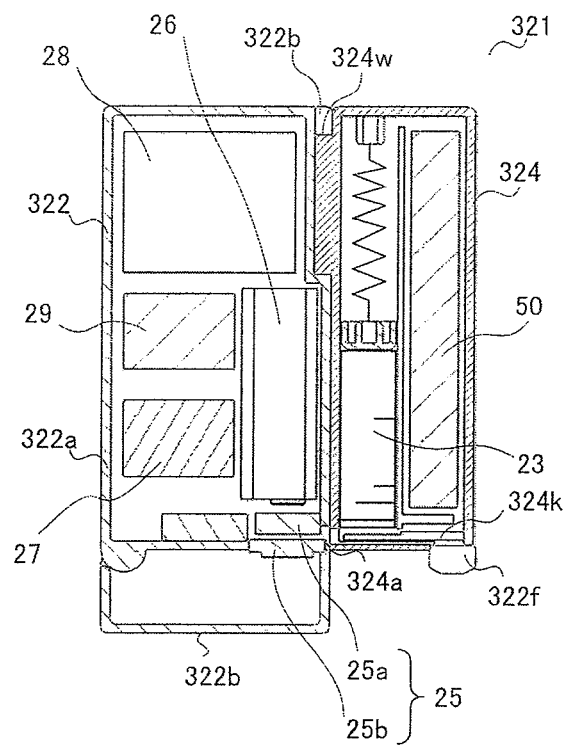
FIG. 39 is a cross sectional view of the blood test apparatus according to embodiment 4 of the present invention.
Figure 40:
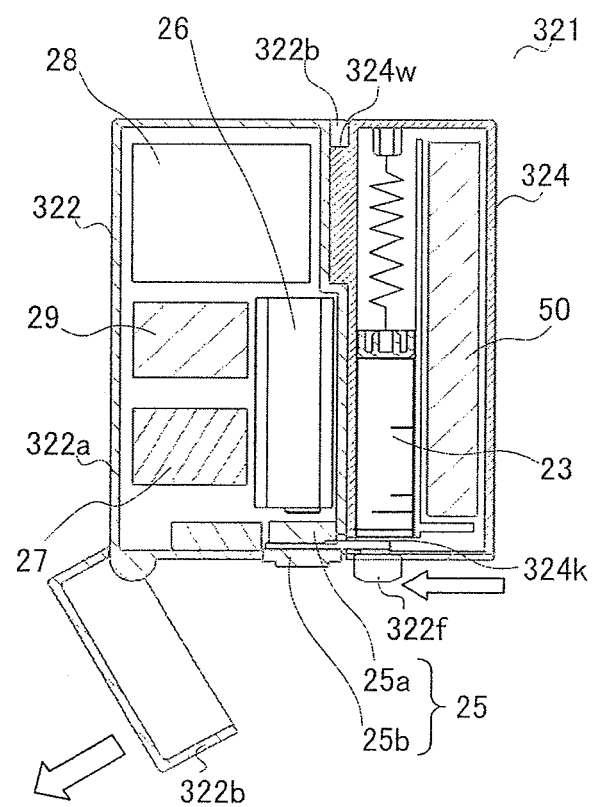
FIG. 40 is a cross sectional view of the blood test apparatus according to embodiment 4 of the present invention.

FIG. 37 and FIG. 38 are perspective views of blood test apparatus 321 according to the preset embodiment. In addition, FIG. 39 and FIG. 40 are cross sectional views of blood test apparatus 321 according to the present embodiment. FIG. 37 shows a state where cartridge 324 is separated from housing 322, and FIG. 38, FIG. 39 and FIG. 40 show a state where cartridge 324 is externally attached to housing 322. FIG. 37, FIG. 38 and FIG. 39 show a state where housing 322 is closed. FIG. 40 shows a state at a time when housing 322 is opened and sensor 23 is inserted in holding section 25.

As shown in FIG. 37, engaging concave part 322p is provided on main body 322a of housing 322, while an engaging convex part 324w is provided on cartridge 324. Engaging concave part 322p is engaged with engaging convex part 324w, so that cartridge 324 is externally fixed to housing 322 as shown in FIG. 38.

In addition, when blood test apparatus 321 is used, the patient first opens cover 322b as shown in FIG. 40, from a state (non-use state) as shown in FIG. 39. By this means, sensor outlet 324a of cartridge 324 opens. Next, the patient slides operation lever 322f toward holding section 25. By this means the undermost one sensor 23 among stacked sensors 23 can be separated, and sensor 23 placed onto slider plate 324k can be conveyed from sensor outlet 324a to holding section 25.

Sensor 23 conveyed from sensor outlet 324a of cartridge 324 is inserted between first holder 25a and second holder 25b.

As described above, according to the present embodiment, the type of blood test apparatus having a cartridge externally attached to the housing can achieve the same effect as embodiment 1.

Embodiment 5

In the present embodiment, an instance for identifying whether a cartridge inserted in the blood test apparatus is new or not will be described. Here, the same components as in embodiment 1 to embodiment 4 will be assigned the same reference numerals and explanation thereof will be simplified.

Embodiment 5-1

Figure 41:
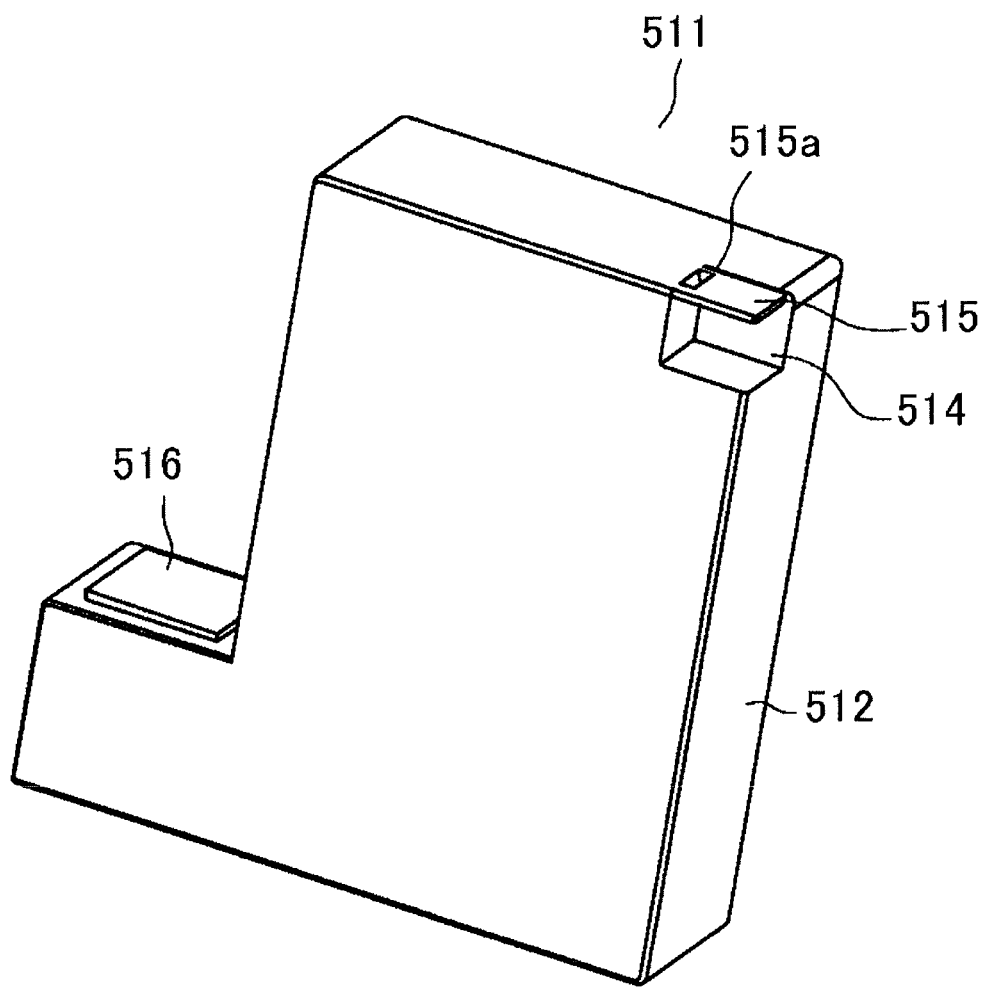
FIG. 41 is an external perspective view of a cartridge according to embodiment 5 of the present invention.

FIG. 41 is an external perspective view of cartridge 511 according to the present embodiment. Concave part 514 is formed on a corner in the upper part of case 512, and tongue part 515 is integrated with case 512 such that tongue part 515 closes the upper end of concave part 514. Tongue section 515 is used as a detected means. Cut part 515a of tongue part 515 is thinned and coupled to case 512 through a removable connecting part.

Figure 42A:
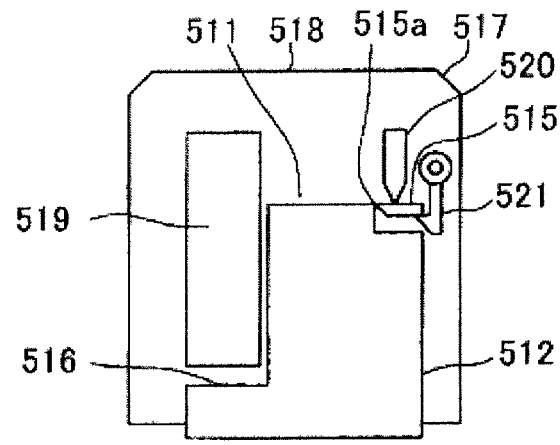
FIG. 42A is a state diagram of a blood test apparatus into which the cartridge is inserted according to embodiment 5 of the present invention.

Next, the operation of tongue part 515 as the detected means will be described with reference to FIG. 42. FIG. 42 is a state diagram showing blood test apparatus 518 in which cartridge 511 is inserted. Cartridge 511 is removably mounted into blood test apparatus 518 from beneath. Laser emitting device 519 faces puncturing section 516 formed in cartridge 511.

When cartridge 511 is inserted in blood test apparatus 518, pawl 521 is inserted in concave part 514 formed on the upper part of cartridge 511 such that pawl 521 abuts on the under side of tongue part 515. This pawl 521 is pivotally attached to housing 517 of blood test apparatus 518. In addition, detecting sensor 520 provided in housing 517 abuts on tongue part 515.

Figure 42B:
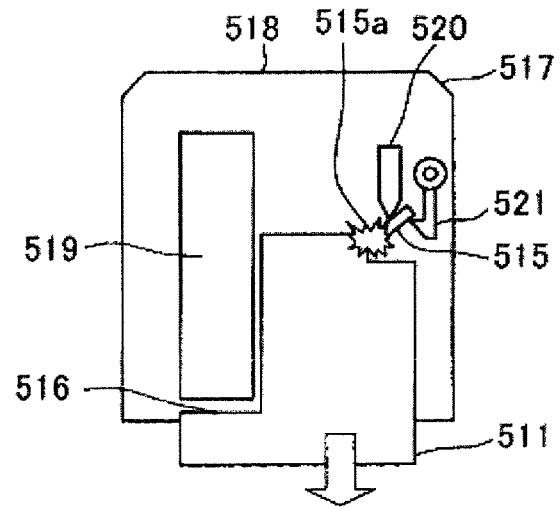
FIG. 42B is a state diagram of the blood test apparatus into which the cartridge is inserted according to embodiment 5 of the present invention.
Figure 42C:
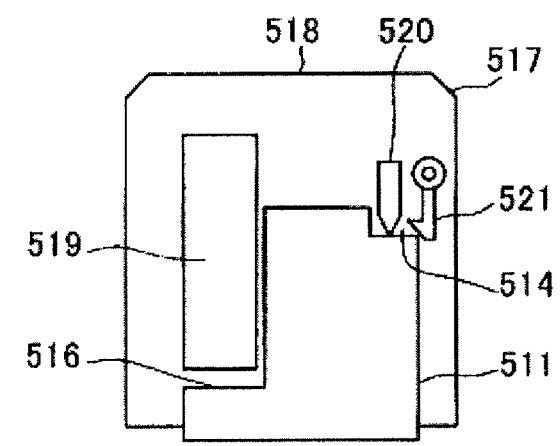
FIG. 42C is a state diagram of the blood test apparatus into which the cartridge is inserted according to embodiment 5 of the present invention.

Next, when the patient attempts to pull cartridge 511 out from housing 517, tongue part 515 is bent at cut part 515a by the operation of pawl 521 and is cut as shown in FIG. 42B. Therefore, it is possible to know that cartridge 511 having tongue part 515 which has been cut is used once. Then, even if cartridge 511 having cut tongue part 515 is inserted in blood test apparatus 518 again, detecting sensor 520 detects the bottom of concave part 514 because tongue part 515 is removed as shown in FIG. 42C.

That is, blood test apparatus 518 can detect that inserted cartridge 511 is not new but a used one which has been inserted once. Here, detecting sensor 520 may be a mechanical switch as with the present embodiment and may be an optical sensor.

As described above, since tongue part 515 on which the usage condition of sensor 23 stored in case 512 is detected is provided, it is possible to easily identify whether cartridge 511 is new or not.

Embodiment 5-2

In the present embodiment, an instance will be described where two types of sensors stacked and stored in the cartridge are prepared, and the difference between the two sensors is electrically detected to detect whether the cartridge is new or not.

Figure 43:
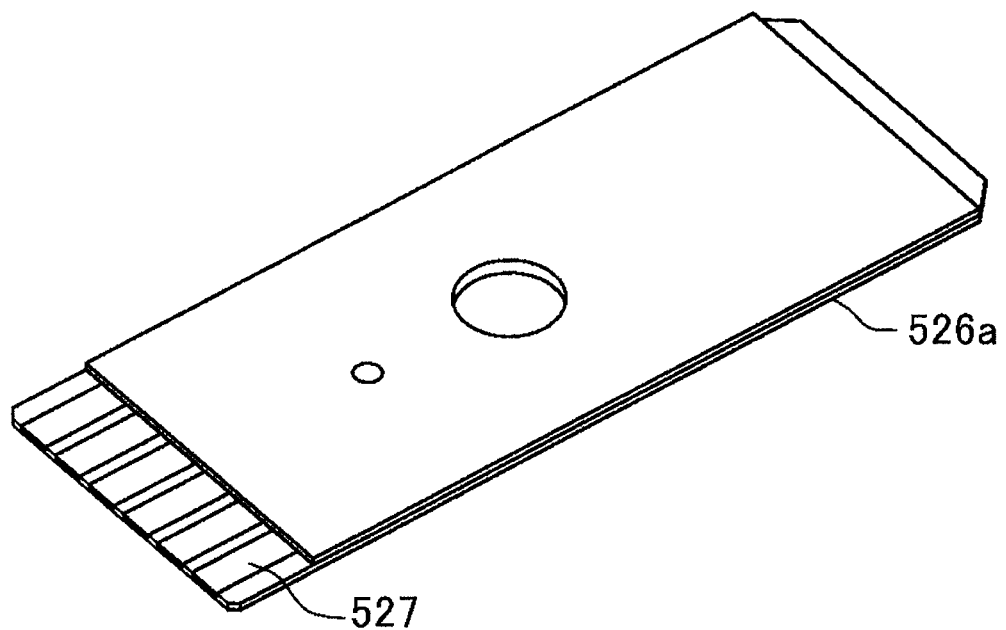
FIG. 43 is an external perspective view of a sensor according to embodiment 5 of the present invention.
Figure 44:
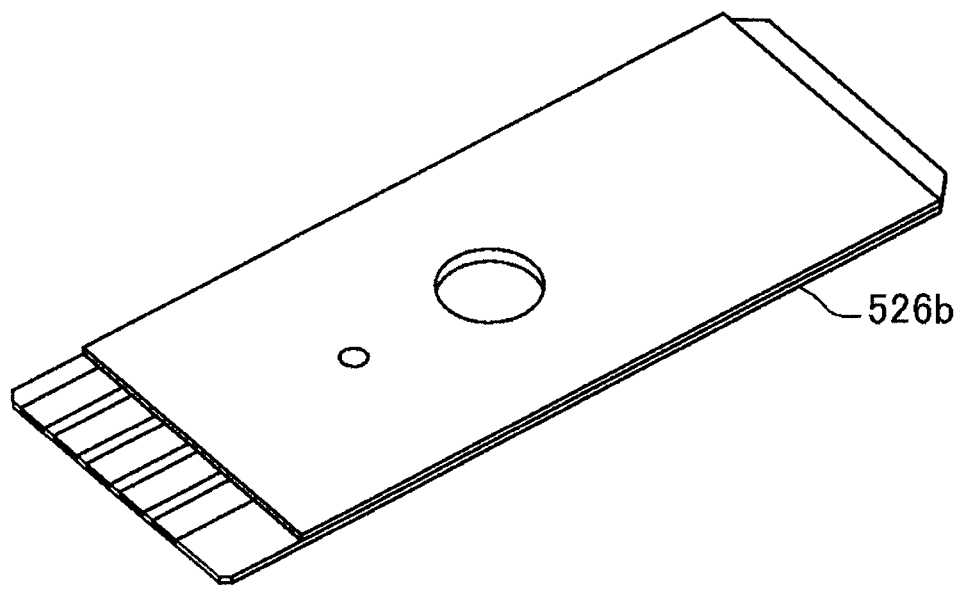
FIG. 44 is an external perspective view of a sensor according to embodiment 5 of the present invention.

FIG. 43 and FIG. 44 are external perspective views of sensors 526a and 526b according to the present embodiment. Sensor 526a shown in FIG. 43 is stored undermost, and sensor 526b is stacked thereon subsequently. Sensor 526a has identification electrode 527 while sensor 526b does not have identification electrode 527.

The blood test apparatus tests, for the sensor conveyed after the cartridge is inserted, whether there is electrical conduction between the connection electrode and identification electrode 527. Then, if so, the blood test apparatus detects that the conveyed sensor is first sensor 526a and the conveyed cartridge is new. Meanwhile, if not so, the blood test apparatus detects that the conveyed sensor is not the first one being sensor 526b and the inserted cartridge is not new.

As described above, the blood test apparatus tests whether the conveyed sensor has identification electrode 527 or not to identify sensor 526a from sensor 526b and detect whether the inserted cartridge is new or not.

In addition, information on the calibration curve to be used can be stored and manufacturing information can be stored by changing the electrical resistivity of the identification electrode 527. Moreover, for a plural types of sensors, the type of the sensor can be determined and thereby the calibration curve can be selected. Therefore, the blood test can be performed more accurately using those information.

Moreover, sensor 526a and sensor 526b can be made of the same material as that of substrate 31, spacer 32 and cover 33. Consequently, the components can be made of the same material and manufactured with the same mold, so that the cost can be reduced.

Embodiment 5-3

Figure 45:
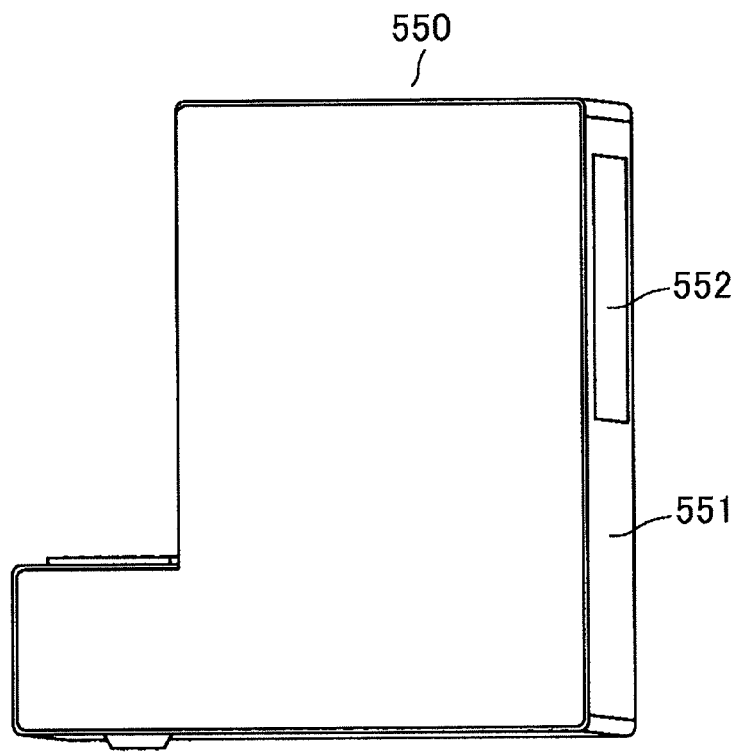
FIG. 45 is an external perspective view of the cartridge according to embodiment 5 of the present invention.

In the present embodiment, an instance where the blood test apparatus detects whether the cartridge is new or not, based on recorded data will be described. Here, the recorded data is obtained by attaching a RF-ID (Radio Frequency Identification) (micro radio chip) or magnetic tape 552 to the outer side of case 551 forming cartridge 550 as shown in FIG. 45.

In this case, the blood test apparatus reads characteristic information, for example, manufacturing information on sensor 23, which is previously recorded on the RF-ID or magnetic tape 552 at a time when cartridge 550 is inserted. In addition, the blood test apparatus writes to the RF-ID or magnetic tape 552 at a time when sensor 23 is separated and ejected. Therefore, it is preferable to attach magnetic tape 552 to the side surface of case 551 in a longitudinal direction in order to easily read and write. Here, the RF-ID may be attached anywhere. Electrical information of the RF-ID or magnetic information of magnetic tape 552 is displayed on the display section of the blood test apparatus, which has a wireless function of the RF-ID or a read/write function of the magnetic tape.

In the present embodiment, data can be recorded as the electrical information or magnetic information, so that the blood test apparatus can detect whether cartridge 550 is new or not, and also can record the time and date of use and the time during which the cartridge is used. By this means, the situation of deterioration and so forth of sensors 23 in cartridge 550 can be understood.

Figure 46:
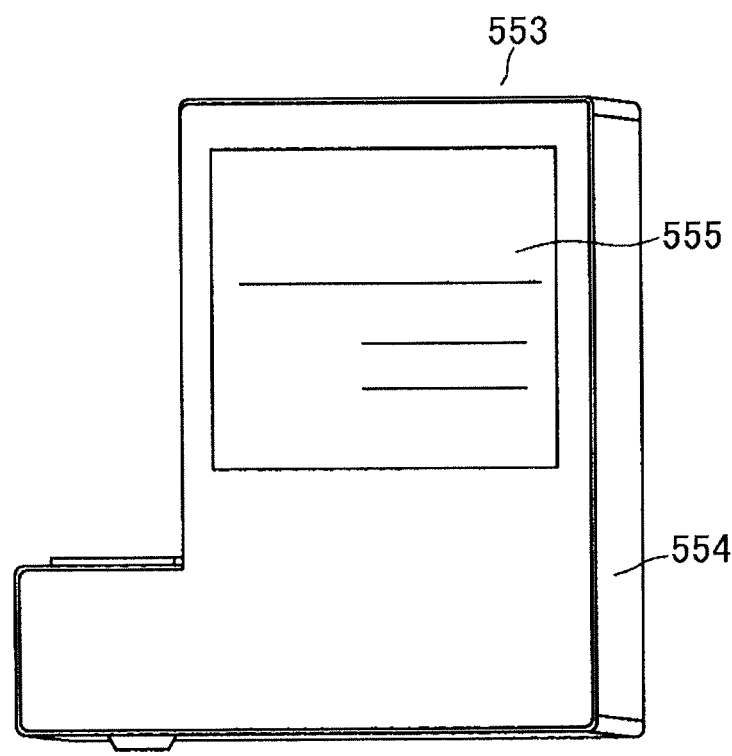
FIG. 46 is an external perspective view of the cartridge according to embodiment 5 of the present invention.

Here, as shown in FIG. 46, writable label 555 may be pasted on the outer side of case 554 forming cartridge 553, and the time and date of inserting, the time and date of removing, the number of cartridge used and so forth are recorded on label 555, therefore the patient can manage the history of cartridge 553 by him/herself, based on the record. In this case, the patient can know information indicating whether cartridge 553 is new or not as well as the usage history of cartridge 553 by visually checking the record of label 555. Here, it is preferred that production management information (serial number, manufacturing date, lot number etc.) on sensors 23 stacked and stored in cartridge 553 is printed on label 555 in characters or in the bar-code format.

Figure 47:
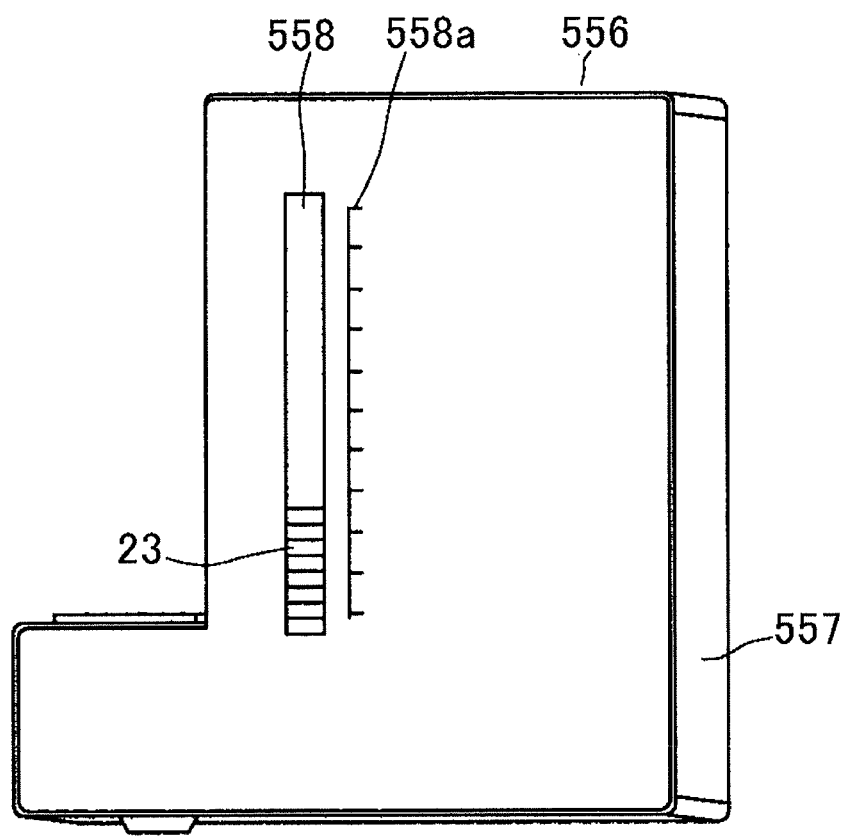
FIG. 47 is an external perspective view of the cartridge according to embodiment 5 of the present invention.

Moreover, as shown in FIG. 47, transparent or translucent window 558 is provided in a slit shape in order to visually check sensors 23 stacked and stored in case 555 forming cartridge 556 and to visually recognize the inside of cartridge 556, so that the patient can directly and visually recognize whether cartridge 553 is new or not. Here, indicator 558a indicating the number of sensors 23 are provided near slit-shaped window 558, so that the patient can easily know the remaining number of sensors 23. In addition, it is more preferable to provide indicators having different colors, where the colors are preferably changed every 10 sensors. Particularly, it is more preferable to provide a red or red-tinged indicator in the position in which the remaining number of sensors is small in order to visually promote to get ready for replacing cartridge 553.

Moreover, each case 512, 551, 554 and 557 forming above-mentioned cartridge 511, 550, 553 and 556 may be made of a dichroic filter having a property that blocks ultraviolet light but passes visible light. Case 512, 551, 554 or 557 does not pass ultraviolet light to prevent sensors 23 stacked and stored from deteriorating, but pass visible light, so that it is possible to easily recognize visually the usage condition of sensors 23 from outside.

The present invention claims priority based on Japanese Patent Application No. 2007-186636, filed on Jul. 18, 2007, Japanese Patent Application No. 2007-186637, filed on Jul. 18, 2007, Japanese Patent Application No. 2007-186638, filed on Jul. 18, 2007, Japanese Patent Application No. 2007-186639, filed on Jul. 18, 2007, Japanese Patent Application No. 2007-186642, filed on Jul. 18, 2007 and Japanese Patent Application No. 2008-006588, filed on Jan. 16, 2008. The disclosure including the specification and drawings as filed, is incorporated herein by reference in its entirety.

INDUSTRIAL APPLICABILITY

The present invention is applicable to a blood test apparatus that punctures skin by using a puncturing means such as a laser emitting device, samples blood exuding from the skin and analyzes the components of the blood.

The invention claimed is:

1. A blood test apparatus that punctures skin and analyzes a property of blood exuding from the skin, comprising:
blood sensors that each have a storing section for storing the blood exuding from the skin;
a conveying unit that is configured to convey a blood sensor from a first position to a second position where the blood is to be stored in the storing section;
a holding unit that is configured to hold the blood sensor in the second position;
a puncturing unit that is configured to puncture the skin while the blood sensor is held in the second position; and
a housing having an opening part comprising the second position, the housing having a cover which is configured to open and close the opening part;
wherein the cover is configured to close the opening part such that a shutter between the first position and the second position closes so as to prevent the blood sensor disposed in the first position from being conveyed to the second position, and
wherein the cover is configured to open the opening part such that the shutter opens so as to allow the blood sensor disposed in the first position to be conveyed to the second position.

2. The blood test apparatus according to claim 1, further comprising:
the housing configured to hold the puncturing unit inside; and
a cartridge that has a sensor chamber in which the blood sensors are stacked and stored, and the cartridge being removably attached to the housing,
wherein the conveying unit is configured to convey the blood sensors from the first position in the sensor chamber to the second position in the housing.

3. The blood test apparatus according to claim 2, wherein the cartridge is housed in the housing.

4. The blood test apparatus according to claim 3, wherein: the cover is configured to seal the cartridge when the opening part is closed.

5. The blood test apparatus according to claim 4, wherein: the cover is configured to move the shutter to close a sensor outlet of the cartridge when the opening part is closed.

6. The blood test apparatus according to claim 4, wherein: the cartridge has a slit hole,
the conveying unit has:
a slider plate that is configured to separate and convey one blood sensor from the blood sensors that are stacked and stored in the cartridge; and
an arm that is fixed to the slider plate and projects from the slit hole provided on the cartridge, and
the cover is configured to cover the slit hole of the cartridge when the opening part is closed.

7. The blood test apparatus according to claim 6, wherein the cover has a fitting part into which the arm of the conveying unit is fitted when the opening part is closed.

8. The blood test apparatus according to claim 4, wherein the cover is pivotally mounted to a main body of the housing and is configured to rest in at least two positions at which the cover is open.

9. The blood test apparatus according to claim 8, further comprising an angle detecting section that is configured to detect an angle in a position at which the cover is open.

10. The blood test apparatus according to claim 2, further comprising a negative pressure unit that is configured to apply a negative pressure,
wherein the cartridge has a negative pressure outlet that is configured to apply the negative pressure of the negative pressure unit to an inside of the sensor chamber.

11. The blood test apparatus according to claim 2, further comprising a pressing section that is configured to press the blood sensors that are stacked and stored, wherein the pressing section has a through-hole that is configured to communicate with the storing section of the blood sensor.

12. The blood sensor apparatus according to claim 2, wherein:

the cartridge has a drying chamber having a desiccant; and the drying chamber is configured to communicate with the sensor chamber.

13. The blood test apparatus according to claim 10, wherein the cartridge has a pressure sensor that is configured to detect an atmospheric pressure of an inside of the cartridge.

14. The blood test apparatus according to claim 2, wherein the negative pressure unit is configured to apply a negative pressure to an inside of the sensor chamber and an inside of the holding unit.

15. The blood test apparatus according to claim 1, wherein the puncturing unit is a laser emitting device that is configured to puncture the skin with laser light.

16. The blood test apparatus according to claim 15, wherein:

the storing section of the blood sensor has a through-hole; and the puncturing unit is configured to allow the laser light to pass through the through-hole of the storing section to puncture the skin.

17. The blood test apparatus according to claim 16, wherein the holding unit has a through-hole having a size configured to allow puncturing in a position facing the through-hole of the storing section while the blood sensor is held in the second position.

18. The blood test apparatus according to claim 15, further comprising a lens protecting member made of a material through which the laser light is configured to be transmitted, the lens protecting member being provided between the puncturing unit and the holding unit.

19. The blood test apparatus according to claim 1, wherein the puncturing unit is a needle puncture device that is configured to puncture the skin with a puncture needle.

20. The blood test apparatus according to claim 19, wherein the storing section of the blood sensor has a through-hole, and the puncturing unit is configured to allow the puncture needle to pass through the through-hole of the storing section to puncture the skin.

21. The blood test apparatus according to claim 20, wherein the holding unit has a though-hole having a size configured to allow puncturing in a position facing the through-hole of the storing section while the blood sensor is held in the second position.

22. The blood test apparatus according to claim 1, wherein a distance from the puncturing unit to a surface of the holding unit where the skin touches is kept constant.

23. The blood test apparatus according to claim 1, wherein the holding unit has a connector that is connected to an electrode provided in the blood sensor.

24. The blood test apparatus according to claim 1, wherein the holding unit includes a first holder and a second holder, and the blood sensor is configured to be sandwiched between the first holder and the second holder in the second position.

25. The blood test apparatus according to claim 24, wherein the holding unit has an elastic member and is configured to bias the second holder toward the first holder by an elastic force of the elastic member to hold the blood sensor.

26. The blood test apparatus according to claim 24, wherein surfaces of the first holder and the second holder are configured to sandwich the blood sensor and are provided on a track on which the blood sensor is configured to be conveyed by the conveying unit.

27. The blood test apparatus according to claim 24, wherein the conveying unit is configured to insert the blood sensor between the first holder and the second holder.

28. The blood test apparatus according to claim 24, wherein the holding unit has a positioning section that is configured to restrict a movement of the blood sensor in a horizontal direction on one of the first holder and the second holder.

29. The blood test apparatus according to claim 1, further comprising a sensor detecting section that is configured to detect when the blood sensor is held by the holding unit, based on an electric property of an electrode provided on the blood sensor.

30. The blood test apparatus according to claim 1, further comprising a skin detecting section that is configured to detect when the skin touches the holding unit.

31. A method for testing the blood test apparatus according to claim 1, comprising a cartridge in which the blood sensors are stacked and stored, the method comprising:

conveying a blood sensor of the blood sensors stored in the cartridge, from a first position in the cartridge to a second position;

puncturing the skin by the puncturing unit while the blood sensor is held in the second position;

storing the blood exuding from the skin in the storing section of the blood sensor; and analyzing a component of the blood on the blood sensor.

* * * * *